(12) United States Patent
Kaula et al.

(10) Patent No.: US 9,072,903 B2
(45) Date of Patent: Jul. 7, 2015

(54) SYSTEM AND METHOD OF ESTABLISHING A PROTOCOL FOR PROVIDING ELECTRICAL STIMULATION WITH A STIMULATION SYSTEM TO TREAT A PATIENT

(75) Inventors: Norbert Kaula, Arvada, CO (US);
Yohannes Iyassu, Denver, CO (US);
Richard J. Polefko, Parma, OH (US);
Steven E. Wilder, Ashland, OH (US);
Scott G. Leyh, Cleveland Heights, OH (US)

(73) Assignee: Greatbatch Ltd., Clarence, NY (US)

( * ) Notice: Subject to any disclaimer, the term of this patent is extended or adjusted under 35 U.S.C. 154(b) by 106 days.

(21) Appl. No.: 13/118,775

(22) Filed: May 31, 2011

(65) Prior Publication Data
US 2012/0310300 A1 Dec. 6, 2012

(51) Int. Cl.
| A61N 1/00 | (2006.01) |
| A61N 1/36 | (2006.01) |
| A61N 1/372 | (2006.01) |
| A61N 1/05 | (2006.01) |
| G06F 19/00 | (2011.01) |

(52) U.S. Cl.
CPC ............ *A61N 1/36125* (2013.01); *A61N 1/0551* (2013.01); *A61N 1/36132* (2013.01); *A61N 1/37247* (2013.01); *G06F 19/3412* (2013.01)

(58) Field of Classification Search
USPC .............................................. 607/46, 59, 60
See application file for complete search history.

(56) References Cited

U.S. PATENT DOCUMENTS

| 6,978,171 | B2 | 12/2005 | Goetz et al. | |
| 7,174,215 | B2* | 2/2007 | Bradley | 607/59 |
| 7,263,402 | B2* | 8/2007 | Thacker et al. | 607/46 |
| 7,881,805 | B2 | 2/2011 | Bradley et al. | |
| 2001/0034542 | A1 | 10/2001 | Mann | |
| 2006/0241722 | A1 | 10/2006 | Thacker et al. | |
| 2006/0253174 | A1* | 11/2006 | King | 607/62 |
| 2006/0293720 | A1 | 12/2006 | DiLorenzo | |
| 2007/0032834 | A1 | 2/2007 | Gliner et al. | |
| 2007/0167991 | A1 | 7/2007 | DiLorenzo | |
| 2007/0255346 | A1 | 11/2007 | Rondoni et al. | |
| 2008/0215118 | A1* | 9/2008 | Goetz et al. | 607/59 |
| 2009/0018617 | A1 | 1/2009 | Skelton et al. | |
| 2009/0118786 | A1 | 5/2009 | Meadows et al. | |
| 2009/0234422 | A1* | 9/2009 | Goetz et al. | 607/66 |
| 2010/0010584 | A1 | 1/2010 | Skelton et al. | |
| 2010/0010585 | A1 | 1/2010 | Davis et al. | |
| 2010/0010589 | A1 | 1/2010 | Skelton et al. | |
| 2010/0023090 | A1 | 1/2010 | Jaax et al. | |

(Continued)

OTHER PUBLICATIONS

Freescale Semiconductor, Inc., "i.MX51 Applications Processors for Consumer and Industrial Products," Data Sheet: Technical Data, Document No. IMX510EC, Rev. 4 (Aug. 2010) 200 pages.

(Continued)

*Primary Examiner* — Niketa Patel
*Assistant Examiner* — William Levicky
(74) *Attorney, Agent, or Firm* — Michael Best & Friedrich LLP

(57) ABSTRACT

A stimulation system, such as a spinal cord stimulation (SCS) system, having a programmer and a patient feedback device for establishing a protocol to treat a patient. The programmer uses a computer assisted stimulation programming procedure for establishing the protocol. Also described are methods of treating a patient with a spinal cord stimulation system including the programmer and the patient feedback device.

21 Claims, 14 Drawing Sheets

(56) References Cited

U.S. PATENT DOCUMENTS

| | | | |
|---|---|---|---|
| 2010/0121408 A1* | 5/2010 | Imran et al. | 607/46 |
| 2010/0268304 A1 | 10/2010 | Matos | |
| 2010/0292556 A1 | 11/2010 | Golden | |
| 2011/0040546 A1 | 2/2011 | Gerber et al. | |
| 2011/0093030 A1* | 4/2011 | Goetz et al. | 607/17 |
| 2012/0310299 A1 | 12/2012 | Kaula et al. | |

OTHER PUBLICATIONS

North, R.B. et al., "Patient-interactive, computer-controlled neurological stimulation system: clinical efficacy in spinal cord stimulator adjustment," J. Neurosurg. (1992) 76(6):967-972, http://www.ncbi.nlm.nih.gov/pubmed/1588431.

Texas Instruments Inc., "Mixed Signal Microcontroller," brochure, MSP430G2x32, MSP430G2x02; SLAS723 (Dec. 2010) 53 pages.

Virtualmedicalcentre.com, "Spinal Cord Stimulation Devices," http://www.virtualmedicalcentre.com/devices.asp?sid=2 (Nov. 1, 2008) 7 pages.

European Search Report for Application No. 12169540.7 dated Sep. 26, 2012 (8 pages).

European Search Report for Application No. 12169540.7 dated Dec. 10, 2012 (2 pages).

United States Patent Office Action for U.S. Appl. No. 13/118,764 dated Dec. 19, 2012 (19 pages).

United States Patent Office Final Rejection for U.S. Appl. No. 13/118,764 dated Jul. 30, 2013 (36 pages).

United States Patent Office Final Rejection for U.S. Appl. No. 13/118,764 dated Jul. 30, 2014 (21 pages).

* cited by examiner

SYSTEM AND METHOD OF ESTABLISHING A PROTOCOL FOR PROVIDING ELECTRICAL STIMULATION WITH A STIMULATION SYSTEM TO TREAT A PATIENT

BACKGROUND

The invention relates to a stimulation system, such as a spinal cord stimulation (SCS) system, having a tool for programming an electrical stimulation generator, such as an implantable pulse generator (IPG), of the system. The invention also relates to a method for developing a protocol for the stimulation system.

A spinal cord stimulator is a device used to provide electrical stimulation to the spinal cord or spinal nerve neurons for managing pain. The stimulator includes an implanted or external pulse generator and an implanted medical electrical lead having one or more electrodes at a distal location thereof. The pulse generator provides the stimulation through the electrodes via a body portion and connector of the lead. Spinal cord stimulation programming is defined as the discovery of the stimulation electrodes and parameters that provide the best possible pain relief (or paresthesia) for the patient using one or more implanted leads and its attached IPG. The programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

With newer medical electrical leads having an increased number of electrodes, the electrode and parameter combination increases exponentially. This results in a healthcare professional, such as a clinician, requiring a substantial amount of time for establishing a manually created protocol for providing therapeutic spinal cord stimulation. Therefore, a manual approach for creating a protocol is not an optimal solution for the SCS system.

SUMMARY

Numerous embodiments of the invention provide a method and system for programming an SCS system with a substantially reduced time requirement and increased accuracy. More specifically, in numerous embodiments, a sweep process is used with the electrodes of an implanted medical lead to determine the proper SCS program (also referred to herein as an SCS protocol) for providing the best possible pain relieve for the patient.

In one embodiment, the invention provides a method of establishing a protocol for providing therapeutic electrical stimulation with a stimulation system for treating a patient. The stimulation system includes an electrical stimulation generator; one or more implanted medical leads coupled to the electrical stimulation generator, the one or more implanted medical leads including a plurality of electrodes; a programmer configured to communicate with the electrical stimulation generator; and a patient feedback device configured to communicate with the programmer. The method includes initiating automated and systematic sweeping of the plurality of electrodes with electrical stimuli provided by the electrical stimulation generator in response to communication from the programmer, determining whether the patient provided feedback with the patient feedback device while performing the automated and systematic sweeping, and creating the protocol for providing therapeutic electrical stimulation to treat the patient based on the automated and systematic sweeping of the plurality of electrodes and the patient provided feedback.

In another embodiment, the invention provides a second method of establishing a protocol for providing therapeutic electrical stimulation with a stimulation system for treating a patient. The method includes performing a first automated and systematic sweep through the plurality of electrodes to determine a respective perception threshold associated with each electrode, detecting patient feedback with the patient feedback device while performing the first automated and systematic sweep, and performing a second automated and systematic sweep through the plurality of electrodes to determine an electrode that is associated with a pain area of the patient. The second automated and systematic sweep uses the respective perception thresholds from the first automated and systematic sweep. The second method further includes detecting patient feedback with the patient feedback device while performing the second automated and systematic sweep, and developing the protocol for providing therapeutic electrical stimulation to treat the patient based on the second automated and systematic sweep and the detected patient feedback.

In another embodiment, the invention provides a method of providing therapeutic treatment to a patient with a spinal cord stimulation system. The stimulation system includes a pulse generator, one or more implanted medical leads having a plurality of electrodes coupled to the pulse generator, a programmer in communication with the pulse generator, and a patient feedback device in communication with the programmer. The method includes storing a location of the patient for implanting the one or more leads to receive stimulation, image capturing an aspect of the one or more leads, and establishing a protocol for the one or more leads with the programmer by performing an automated and systematic sweep through the plurality of electrodes.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The invention herein relates to an electrical stimulation system for providing stimulation to target tissue of a patient. The system described in detail below is a spinal cord stimulation (SCS) system for providing electrical pulses to the neurons of the spinal cord of a patient. However, many aspects of the invention are not limited to spinal cord stimulation. The electrical stimulation system may provide stimulation to other body portions including a muscle or muscle group, nerves, the brain, etc.

Figure 1:
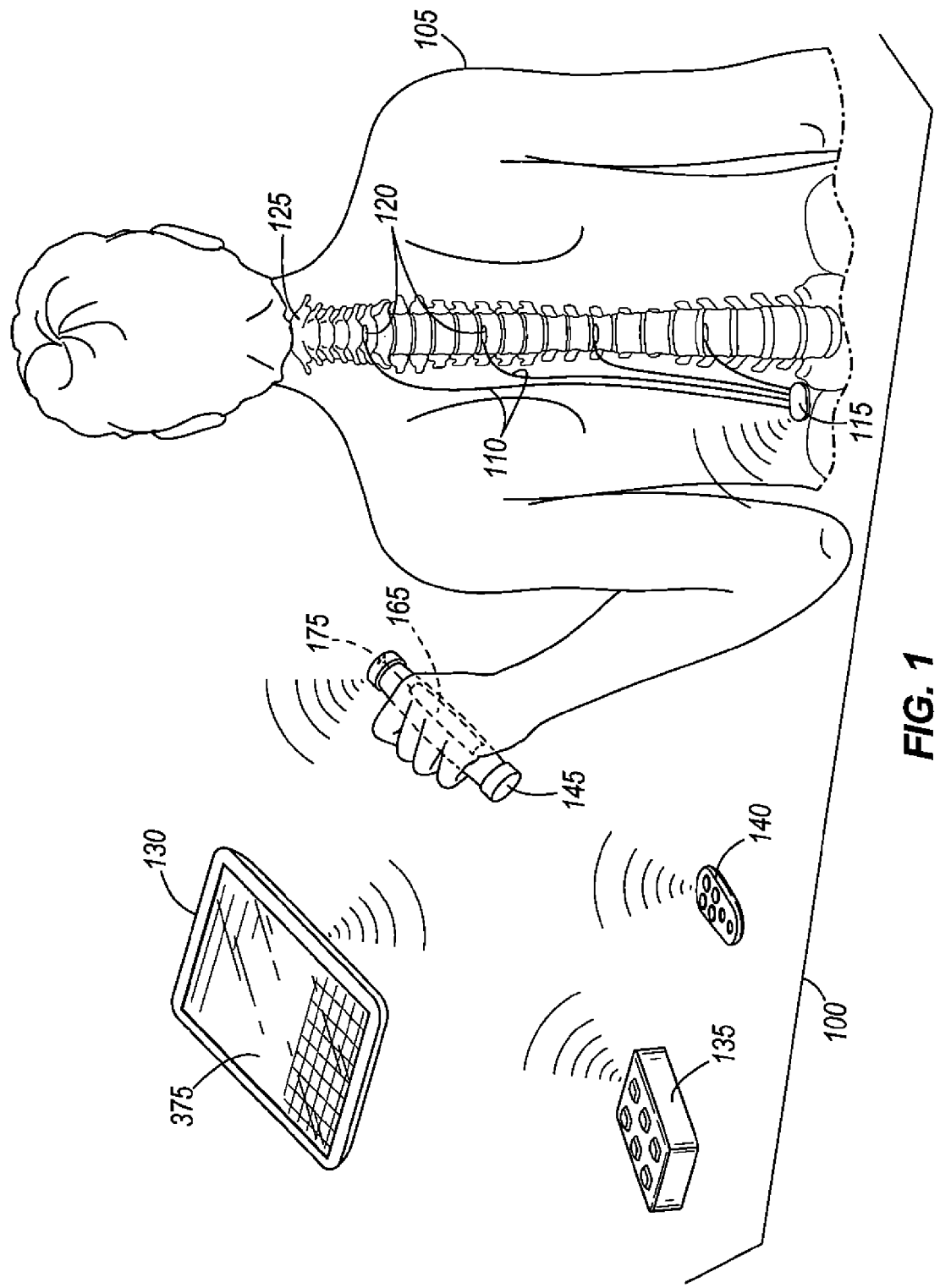
FIG. 1 is a partial perspective view of a patient using a spinal cord stimulation system.

FIG. 1 shows a spinal cord stimulation system 100 in use with a patient 105. The system includes one or more implanted medical electrical leads 110 connected to an implantable pulse generator (IPG) 115. The leads 110 include an electrode array 120 at a distal end of the base lead cable. The electrode array 120 includes one or more electrical stimulation electrodes (may also be referred as electrode contacts or simply electrodes) and is placed adjacent to the dura of the spine 125 using an anchor. The spinal column includes the C1-C7 (cervical), T1-T12 (thoracic), L1-L5 (lumbar) and S1-S6 (sacral) vertebrae and the electrode array(s) 120 may be positioned anywhere along the spine 125 to deliver the intended therapeutic effects of spinal cord electrical stimulation in a desired region of the spine. The electrodes (discussed further in FIGS. 2 and 3) of the electrode arrays 120 promote electrical stimulation to the neurons of the spine based on electrical signals generated by the IPG 115. In one construction, the electrical signals are regulated current pulses that are rectangular in shape. However, the electrical signals can be other types of signals, including other types of pulses (e.g., regulated voltage pulses), and other shapes of pulses (e.g., trapezoidal, sinusoidal). The stimulation is provided from the IPG 115 to the electrodes via the base lead, which is connected to the IPG 115 with the proximal end of the base lead. The body of the lead can traverse through the body of the patient via the spinal column and from the spinal column through the body of the patient to the implant site of the IPG 115.

The IPG 115 generates the electrical signals through a multiplicity of electrodes (e.g., four, eight, sixteen, twenty-four electrodes). The IPG 115 can control six aspects of electrical stimulation based on a protocol (may also be referred to as a program): on/off, amplitude (e.g., current or voltage), frequency, pulse width, pulse shape, and polarity (anodic or cathodic stimulation). The stimulation most discussed herein is a regulated (or constant) current that provides a square wave, cathodic stimulation with a variable amplitude, frequency, and/or pulse width. Typically, the IPG 115 is implanted in a surgically made pocket (e.g., in the abdomen) of the patient. However, the pulse generator can also be an external pulse generator (EPG).

The IPG 115 communicates with any one of a clinician programmer (CP) 130, a patient programmer and charger (PPC) 135, and a pocket (or fob) programmer (PP) 140. As discussed in further detail below, the CP 130 interacts with the IPG 115 to develop a protocol for stimulating the patient. The developing of the protocol is assisted with the use of a patient-feedback device (PFD) 145. Once a protocol is developed, the PPC 135 or the PP 140 can activate, deactivate, or perform limited changes to the programming parameters of the protocol. The protocol may be stored at the IPG 115 or can be communicated and stored at the PPC 135 or the PP 140. The PPC 135 is also used for charging the IPG 115.

For the construction described herein, the IPG 115 includes a rechargeable, multichannel, radio-frequency (RF) programmable pulse generator housed in a metallic (e.g., titanium) case or housing. The metallic case is sometimes referred to as the "can" and may act either as a cathode or an anode or floating to the electrical contacts.

Figure 2:
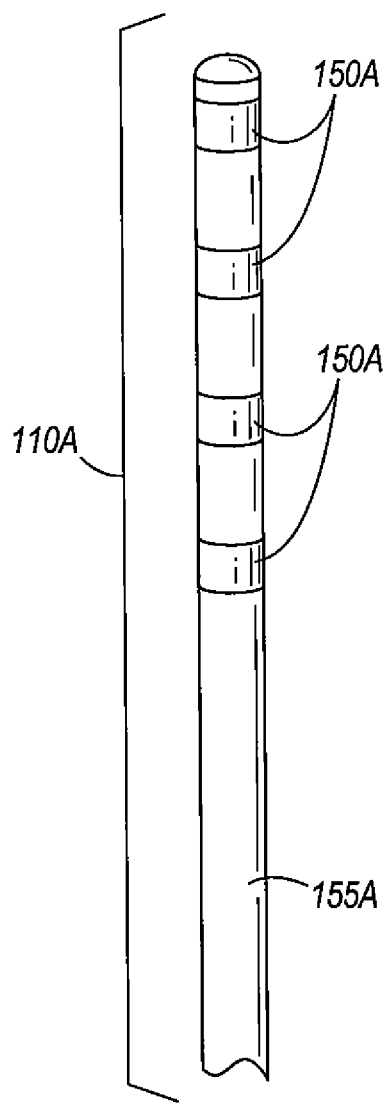
FIG. 2 is a perspective view of an in-line lead for use in the spinal cord stimulation system of FIG. 1.
Figure 3:
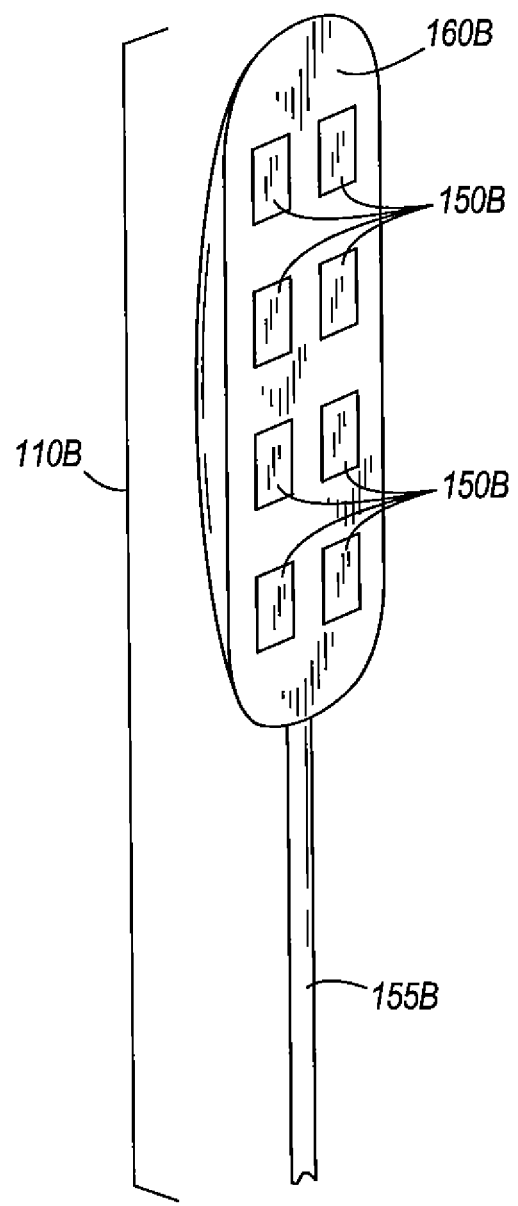
FIG. 3 is a perspective view of a paddle lead for use in the spinal cord stimulation system of FIG. 1.

Referring now to FIGS. 2 and 3, the figures show two exemplary leads 110A and 110B, respectively, that can be used in the SCS system. A first common type of lead 110 is the "in-line" lead shown in FIG. 2. An in-line lead 110A includes individual electrodes 150A along the length of a flexible cable 155A. A second common type of lead 110 is the "paddle" lead shown in FIG. 3. In general, the paddle lead 110B is shaped with a wide platform 160B on which a variety of electrode 150B configurations are situated. For example, the paddle lead 110B shown in FIG. 3 has two columns of four rectangular shaped electrodes 150B. A paddle lead typically contains contacts on one side only, but is not restricted to individual electrodes on either side, or electrodes perforating the carrier material.

For both leads shown in FIGS. 2 and 3, a flexible cable 155A or 155B has respective small wires for the electrodes 150A or 150B. The wires are embedded within the cable 155A or 155B and carry the electrical stimulation from the IPG 115 to the electrodes 150A or 150B.

It is envisioned that other types of leads 110 and electrode arrays 120 can be used with the invention. Also, the number of electrodes 150 and how the electrodes 150 are arranged in the electrode array 120 can vary from the examples discussed herein.

The leads shown in FIGS. 2 and 3 are multiple channel leads. Here, a "channel" is defined as a specified electrode 150, or group of electrodes 150, that receives a specified pattern or sequence of electrical stimuli. For simplicity, this description will focus on each electrode 150 and the IPG's 115 metallic housing providing a respective channel. When more than one channel is available, each channel may be programmed to provide its own stimulus to its defined electrode.

There are many instances when it is advantageous to have multiple channels for stimulation. For example, different pain locations (e.g., upper extremities, lower extremities) of the patient may require different stimuli. Further, some patients may exhibit conditions better suited to "horizontal" stimulation paths, while other patients may exhibit conditions better suited to "vertical" stimulation paths. Therefore, multiple electrodes positioned to provide multiple channels can cover more tissue/neuron area, and thereby provide better stimulation protocol flexibility to treat the patient.

It is also envisioned that the number of leads 110 can vary. For example, one, two, or four leads 110 can be connected to the IPG 115. The electrode arrays 120 of the leads 110, respectively, can be disposed in different vertical locations on the spine 125 with respect to a vertical patient 105, can be disposed horizontally (or "side-by-side") on the spine 125 with respect to a vertical patient 105, or some combination thereof.

In alternative to the IPG 115, the leads 110 can receive electrical stimuli from an external pulse generator (EPG) (also referred to a trial stimulator) through one or more percutaneous lead extensions. An EPG may be used during a trial period.

For the specific construction and operation described herein, a single lead 110 having a two-by-four electrode paddle (as shown in FIG. 3) is secured to the thoracic portion of the spine 125. An IPG 115 having a metallic housing is disposed within the patient 105. The housing acts as another electrode in this contemplated SCS system 100. Thus, this arrangement results in nine electrodes total. Also, the specifically-discussed system includes nine channels formed by the eight electrodes of the electrode array 120, respectively, and the metallic housing of the IPG 115. However, it contemplated that a different number of leads, electrodes, and channels fall within the scope of the invention.

Referring back to FIG. 1, a user provides feedback to the CP 130 with a PFD 145 while the CP 130 develops the protocol for the IPG 115. In FIG. 1, the PFD 145 is an ergonomic handheld device having a sensor (also referred to as input) 165, a controller, and a communications output 175. The sensor 165 can take the form of a discrete switch or can take the form of a continuously variable input, such as through the use of a strain gauge. It is envisioned that the use of a continuously variable input can provide magnitude information, thereby providing feedback information.

Figure 4:
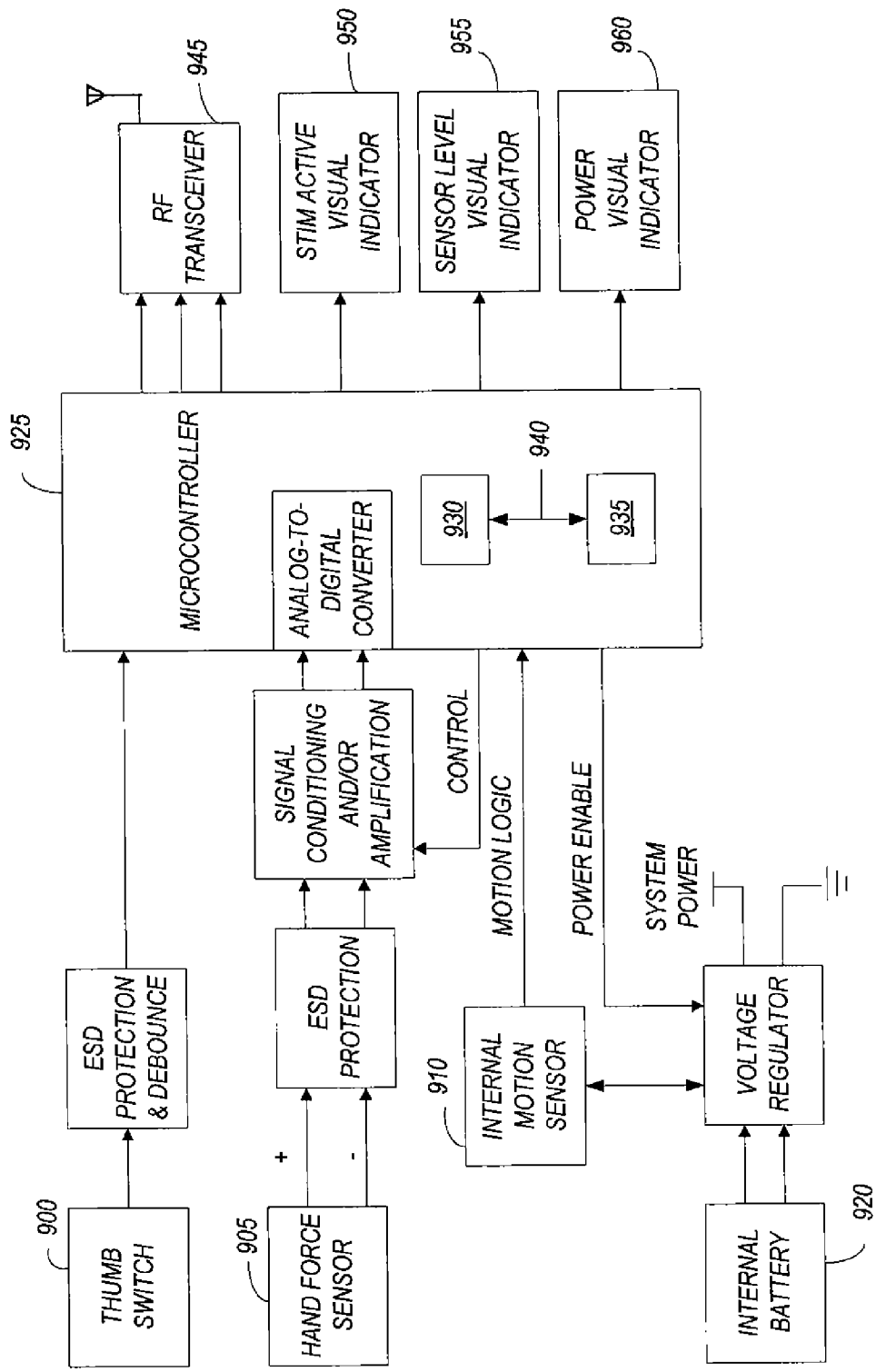
FIG. 4 is a block diagram of a patient-feedback device for use in the spinal cord stimulation system of FIG. 1.

FIG. 4 provides a block diagram of an exemplary handheld PFD 145 used in the SCS system 100. The PFD 145 includes two inputs 900 and 905 in communication with the housing of the device 145 and one input 910 internal to the housing. One of the external inputs 900 is a binary ON/OFF switch, preferably activated by the patient's thumb, to allow the patient 105 to immediately deactivate stimulation. The second input 905 includes a force or displacement sensor sensing the pressure or force exerted by the patient's hand. The sensed parameter can be either isotonic (constant force, measuring the distance traversed) or isometric (measuring the force, proportional to pressure applied by patient 105). The resulting signal from the sensor 905 is analog and, therefore, the signal is conditioned, amplified, and passed to a microcontroller via an analog-to-digital converter.

The internal input 910 for the PFD 145 of FIG. 4 is a motion sensor. The sensor 910, upon detecting motion, initiates activation of the PFD 145. The device 145 stays active until movement is not detected by the sensor 910 for a time period. Power is provided by an internal battery 920 that can be replaceable and/or rechargeable.

The processing of the inputs from the sensors 900 and 905 take place in a controller, such as a microcontroller 925. The microcontroller 925 includes a suitable programmable portion 930 (e.g., a microprocessor or a digital signal processor), a memory 935, and a bus 940 or other communication lines. Output data of the microcontroller 925 is sent via a Bluetooth bi-direction radio communication portion 945 to the CP 130. The Bluetooth portion 945 includes a Bluetooth communication interface, an antenna switch, and a related antenna, all of which allows wireless communication following the Bluetooth Special Interest Group standard. Other outputs may include indicators (such as light-emitting diodes) for communicating stimulation activity 950, sensor activation 955, and device power 960, and a speaker and related circuitry 965 for audible communication.

As discussed further below, the patient 105 provides feedback to the SCS system 100, and specifically the CP 130, while the CP 130 establishes the protocol for the IPG 115. The patient 105 can activate the PFD 145 when the patient 105 feels various stimuli, such as paresthesia or pain.

Figure 5:
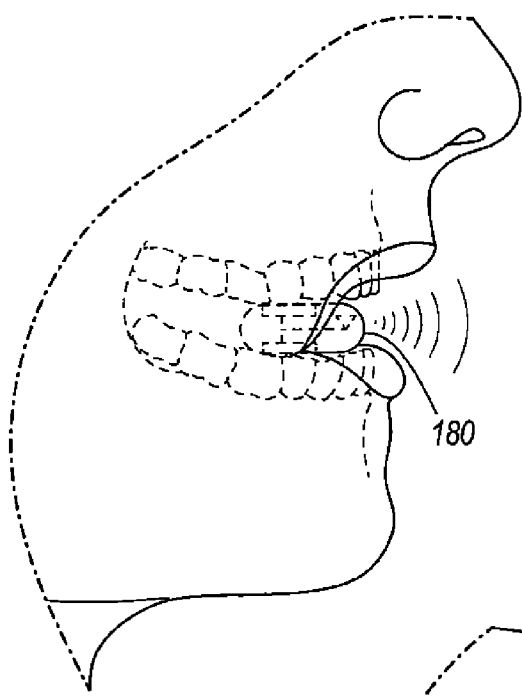
FIG. 5 is a side view of a patient-feedback device inserted in the mouth of a patient
Figure 6:
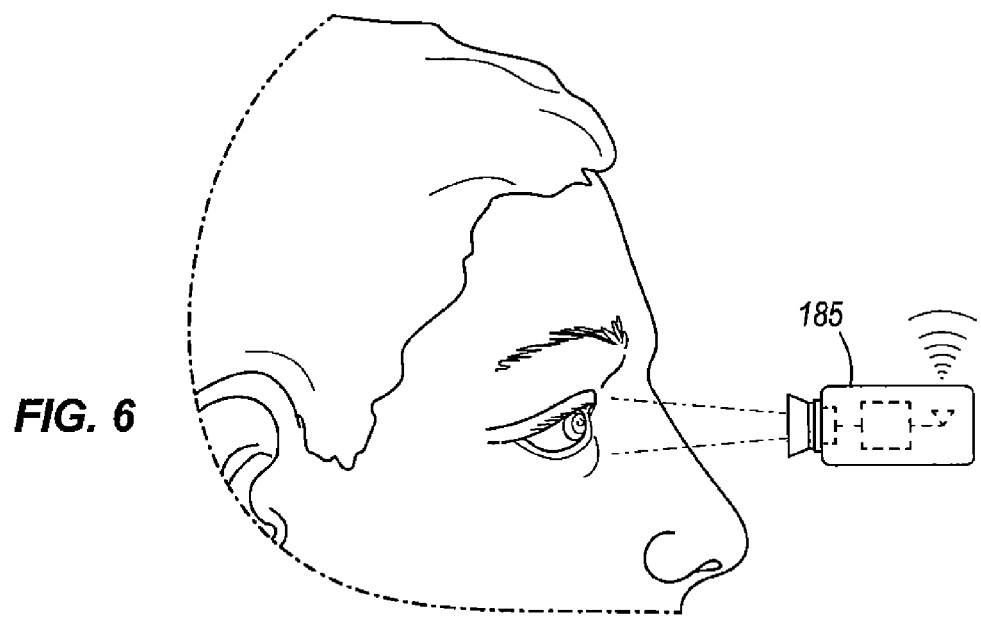
FIG. 6 is a side view of a patient-feedback device with optical sensing.
Figure 7:
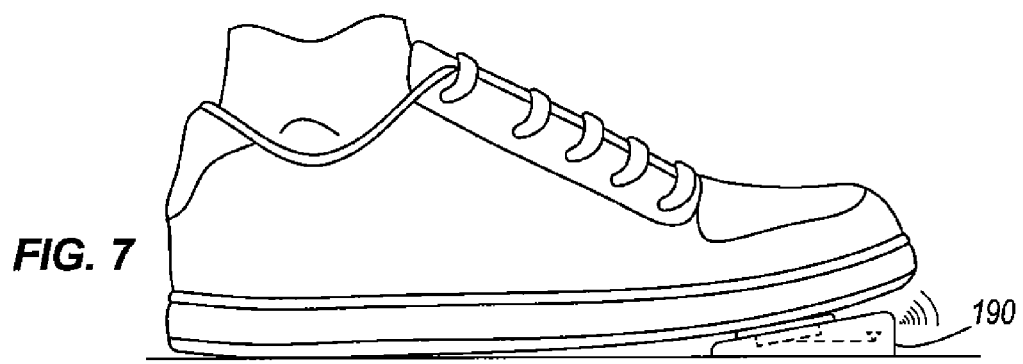
FIG. 7 is a side view of a patient-feedback device activated by a foot of a patient.

FIGS. 5-7 provide other means for receiving patient feedback. More specifically, FIG. 5 shows a mouth-piece 180 that is inserted into the mouth of the patient. The user provides feedback by biting the mouthpiece. FIG. 6 shows an optical sensor 185 (such as a camera and related image processing software) that detects visual cues from a patient. An example visual cue may be the blinking of the patient's eyes. FIG. 7 shows a foot pedal 190 that receives input by the patient manipulating a switch with his foot. It is also envisioned that the patient may provide feedback directly through the touch screen or hard buttons on the CP 130.

As discussed earlier, it should be understood that aspects of the SCS system 110 can be applied to other types of electrical stimulation systems. That is, other electrical stimulation systems provide electrical stimuli to other types of target tissues. Similar to the SCS system 110, these other electrical stimulation systems include one or more medical electrical leads having electrodes, a stimulation generator coupled to the one or more medical electrical leads, and a clinician programmer for establishing a protocol with the stimulation generator.

Figure 8:
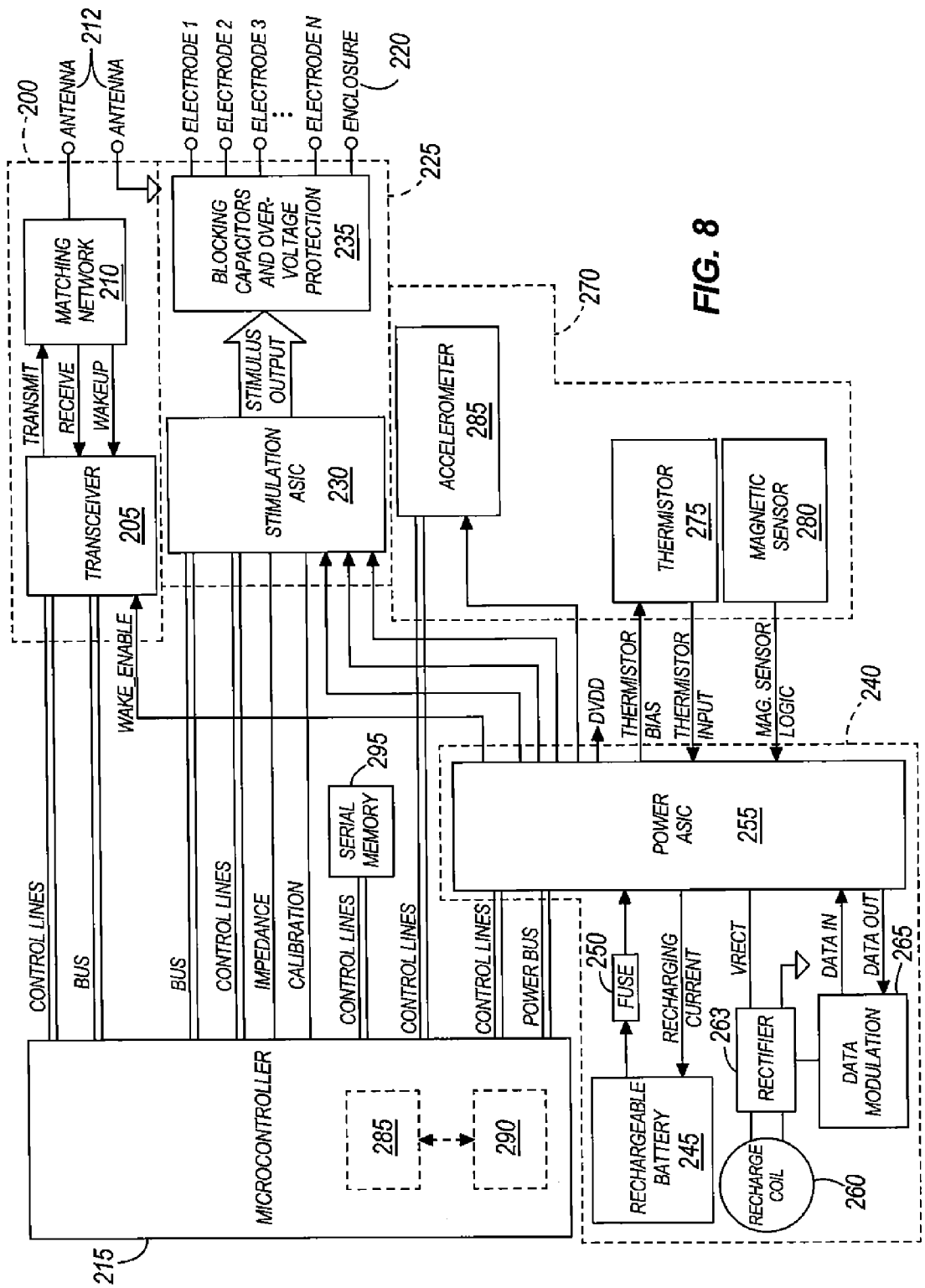
FIG. 8 is a block diagram of an implantable pulse generator for use in the spinal cord stimulation system of FIG. 1.

FIG. 8 shows a block diagram of one construction of the IPG 115. The IPG 115 includes a printed circuit board ("PCB") that is populated with a plurality of electrical and electronic components that provide power, operational control, and protection to the IPG 115. With reference to FIG. 8, the IPG 115 includes a communication portion 200 having a transceiver 205, a matching network 210, and antenna 212. The communication portion 200 receives power from a power ASIC (discussed below), and communicates information to/from the microcontroller 215 and a device (e.g., the CP 130) external to the IPG 115. For example, the IPG 115 can provide bi-direction radio communication capabilities, including Medical Implant Communication Service (MICS) bi-direction radio communication following the MICS specification.

The IPG 115, as previously discussed, provides stimuli to electrodes 150 of an implanted medical electrical lead 110. As shown in FIG. 8, N electrodes 150 are connected to the IPG 115. In addition, the enclosure or housing 220 of the IPG 115 can act as an electrode. The stimuli are provided by a stimulation portion 225 in response to commands from the microcontroller 215. The stimulation portion 225 includes a stimulation application specific integrated circuit (ASIC) 230 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 230 can include a processor, memory, and firmware for storing preset pulses and protocols that can be selected via the microcontroller 215. The providing of the pulses to the electrodes 150 is controlled through the use of a waveform generator and amplitude multiplier of the stimulation ASIC 230, and the blocking capacitors and overvoltage protection circuitry of the stimulation portion 225, as is known in the art. The stimulation portion 225 of the IPG 115 receives power from the power ASIC (discussed below). The stimulation ASIC 230 also provides signals to the microcontroller 215. More specifically, the stimulation ASIC 230 can provide impedance values for the channels associated with the electrodes 150, and also communicate calibration information with the microcontroller 215 during calibration of the IPG 115.

The IPG 115 also includes a power supply portion 240. The power supply portion includes a rechargeable battery 245, fuse 250, power ASIC 255, recharge coil 260, rectifier 263 and data modulation circuit 265. The rechargeable battery 245 provides a power source for the power supply portion 240. The recharge coil 260 receives a wireless signal from the PPC 135. The wireless signal includes an energy that is converted and conditioned to a power signal by the rectifier 263. The power signal is provided to the rechargable battery 245 via the power ASIC 255. The power ASIC 255 manages the power for the IPG 115. The power ASIC 255 provides one or more voltages to the other electrical and electronic circuits of the IPG 155. The data modulation circuit 265 controls the charging process.

The IPG also includes a magnetic sensor 280. The magnetic sensor 280 provides a "hard" switch upon sensing a magnet for a defined period. The signal from the magnetic sensor 280 can provide an override for the IPG 115 if a fault is occurring with the IPG 115 and is not responding to other controllers.

The IPG 115 is shown in FIG. 8 as having a microcontroller 215. Generally speaking, the microcontroller 215 is a controller for controlling the IPG 115. The microcontroller 215 includes a suitable programmable portion 285 (e.g., a microprocessor or a digital signal processor), a memory 290, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at its website; the content of the data sheet being incorporated herein by reference.

The IPG 115 includes memory, which can be internal to the control device (such as memory 290), external to the control device (such as serial memory 295), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 285 executes software that is capable of being stored in the RAM (e.g., during execution), the ROM (e.g., on a generally permanent basis), or another non-transitory computer readable medium such as another memory or a disc.

Software included in the implementation of the IPG 115 is stored in the memory 290. The software includes, for example, firmware, one or more applications, program data, one or more program modules, and other executable instructions. The programmable portion 285 is configured to retrieve from memory and execute, among other things, instructions related to the control processes and methods described below for the IPG 115. For example, the programmable portion 285 is configured to execute instructions retrieved from the memory 290 for sweeping the electrodes 150 in response to a signal from the CP 130.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Figure 9:
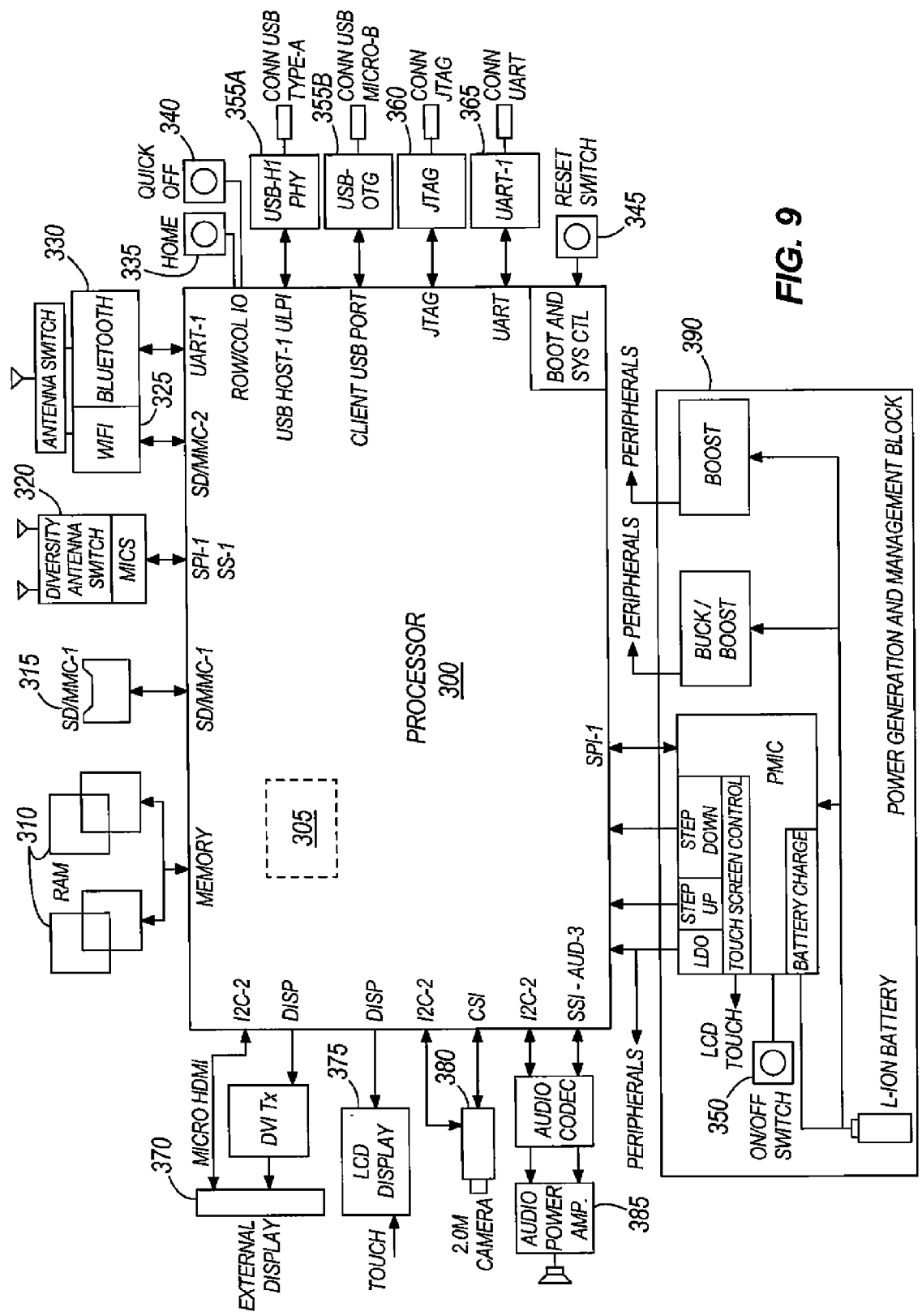
FIG. 9 is a block diagram of a clinician programmer for use in the spinal cord stimulation system of FIG. 1.

FIG. 9 shows a block diagram of one construction of the CP 130. The CP 130 includes a printed circuit board ("PCB") that is populated with a plurality of electrical and electronic components that provide power, operational control, and protection to the CP 130. With reference to FIG. 9, the CP includes a processor 300. The processor 300 is a controller for controlling the CP 130 and, indirectly, the IPG 115 as discussed further below. In one construction, the processor 300 is an applications processor model i.MX515 available from Freescale Semiconductor. More specifically, the i.MX515 applications processor has internal instruction and data cashes, multimedia capabilities, external memory interfacing, and interfacing flexibility. Further information regarding the i.MX515 applications processor can be found in, for example, the "IMX510EC, Rev. 4" data sheet; dated August 2010; published by Freescale Semiconductor at its website, the content of the data sheet being incorporated herein by reference. Of course, other processing units, such as other microprocessors, microcontrollers, digital signal processors, etc., can be used in place of the processor 300.

The CP 130 includes memory, which can be internal to the processor 300 (e.g., memory 305), external to the processor 300 (e.g., memory 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM (e.g., during execution), the ROM (e.g., on a generally permanent basis), or another non-transitory computer readable medium such as another memory or a disc. The CP 130 also includes input/output ("I/O") systems that include routines for transferring information between components within the processor 300 and other components of the CP 130 or external to the CP 130.

Software included in the implementation of the CP 130 is stored in the memory 305 of the processor 300, RAM 310, ROM 315, or external to the CP 130. The software includes, for example, firmware, one or more applications, program data, one or more program modules, and other executable instructions. The processor 300 is configured to retrieve from memory and execute, among other things, instructions related to the control processes and methods described below for the CP 130. For example, the processor 300 is configured to execute instructions retrieved from the memory 140 for establishing a protocol to control the IPG 115.

One memory shown in FIG. 9 is memory 310, which can be a double data rate (DDR2) synchronous dynamic random access memory (SDRAM) for storing data relating to and captured during the operation of the CP 130. In addition, a secure digital (SD) multimedia card (MMC) can be coupled to the CP for transferring data from the CP to the memory card via slot 315. Of course, other types of data storage devices can be used in place of the data storage devices shown in FIG. 9.

The CP 130 includes multiple bi-directional radio communication capabilities. Specific wireless portions included with the CP 130 are a Medical Implant Communication Service (MICS) bi-direction radio communication portion 320, a WiFi bi-direction radio communication portion 325, and a Bluetooth bi-direction radio communication portion 330. The MICS portion 320 includes a MICS communication interface, an antenna switch, and a related antenna, all of which allows wireless communication using the MICS specification. The WiFi portion 325 and Bluetooth portion 330 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP 130.

The CP 130 includes three hard buttons: a "home" button 335 for returning the CP to a home screen for the device, a "quick off" button 340 for quickly deactivating stimulation IPG, and a "reset" button 345 for rebooting the CP 130. The CP 130 also includes an "ON/OFF" switch 350, which is part of the power generation and management block (discussed below).

The CP 130 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 9.

Another device connectable to the CP 130, and therefore supported by the CP 130, is an external display. The connection to the external display can be made via a micro High-Definition Multimedia Interface (HDMI) 370, which provides a compact audio/video interface for transmitting uncompressed digital data to the external display. The use of the HDMI connection 370 allows the CP 130 to transmit video (and audio) communication to an external display. This may be beneficial in situations where others (e.g., the surgeon) may want to view the information being viewed by the healthcare professional. The surgeon typically has no visual access to the CP 130 in the operating room unless an external screen is provided. The HDMI connection 370 allows the surgeon to view information from the CP 130, thereby allowing greater communication between the clinician and the surgeon. For a specific example, the HDMI connection 370 can broadcast a high definition television signal that allows the surgeon to view the same information that is shown on the LCD (discussed below) of the CP 130.

The CP 130 includes a touch screen I/O device 375 for providing a user interface with the clinician. The touch screen display 375 can be a liquid crystal display (LCD) having a resistive, capacitive, or similar touch-screen technology. It is envisioned that multitouch capabilities can be used with the touch screen display 375 depending on the type of technology used.

The CP 130 includes a camera 380 allowing the device to take pictures or video. The resulting image files can be used to document a procedure or an aspect of the procedure. For example, the camera 380 can be used to take pictures of barcodes associated with the IPG 115 or the leads 120, or documenting an aspect of the procedure, such as the positioning of the leads. Similarly, it is envisioned that the CP 130 can communicate with a fluoroscope or similar device to provide further documentation of the procedure. Other devices can be coupled to the CP 130 to provide further information, such as scanners or RFID detection. Similarly, the CP 130 includes an audio portion 385 having an audio codec circuit, audio power amplifier, and related speaker for providing audio communication to the user, such as the clinician or the surgeon.

The CP 130 further includes a power generation and management block 390. The power block 390 has a power source (e.g., a lithium-ion battery) and a power supply for providing multiple power voltages to the processor, LCD touch screen, and peripherals.

As best shown in FIG. 1, the CP 130 is a handheld computing tablet with touch screen capabilities. The tablet is a portable personal computer with a touch screen, which is typically the primary input device. However, an external keyboard or mouse can be attached to the CP 130. The tablet allows for mobile functionality not associated with even typical laptop personal computers.

In operation, the IPG 115 (which may also be an EPG) through the use of the implanted medical electrical leads 110, and specifically the electrodes 150, stimulates neurons of the spinal cord 125. The IPG 115 selects an electrode stimulating configuration, selects a stimulation waveform, regulates the amplitude of the electrical stimulation, controls the width and frequency of electrical pulses, and selects cathodic or anodic stimulation. This is accomplished by a healthcare professional (e.g., a clinician), using the CP 130, setting the parameters of the IPG 115. The setting of parameters of the IPG results in a "program," which is also referred to herein as a "protocol," for the electrode stimulation. Programming may result in multiple protocols that the patient can choose from. Multiple protocols allows, for example, the patient to find a best setting for paresthesia at a particular time of treatment.

With reference to FIG. 3, an electrode array 120 includes eight electrodes 150B. The shown electrode array 120 has two columns and four rows as viewed along a longitude length of the lead 110. More generically, the lead includes cl columns and r rows, where cl is two and r is four. When referring to a particular column, the column is referred to herein as the j-th column, and when referring to a particular row, the row is referred to as the i-th row.

Before proceeding further, it should be understood that not all electrode arrays 120 are conveniently shaped as a simple matrix having definite columns and definite rows. More complex configurations are possible, which are referred to herein as complex electrode array configurations. The processes discussed herein can account for complex electrode array configurations. For example, a representative array having cl columns and r rows for a complex electrode array configuration may include "dummy" addresses having "null" values in the array. For a specific example, an electrode contact may span multiple columns. The resulting array may have a first address i, j representing the multiple column electrode and a second address i, j+1 having a "null" value to account for the multiple columns of the multiple column electrode. This concept can be expanded to even more complex arrangements. Accordingly, all electrode arrays 120 can be addressed as a matrix and it will be assumed herein that the electrode array 120 has been addressed as a matrix.

One process of selecting a best protocol for providing electrical stimulation includes four sub-processes. The processes are referred to herein as the impedance sweep of electrodes, the perception-threshold sweep, the pain-coverage sweep, and the parameter fine adjustment. The selecting of a best protocol occurs during a method of treating a patient with spinal cord stimulation. FIGS. 10-15 provide multiple flow diagrams relating to the treatment of the patient 105 using the SCS 100.

Before proceeding further, it should be understood that the steps discussed in connection with FIGS. 10-15 will be discussed in an iterative manner for descriptive purposes. Various steps described herein with respect to the process of FIGS. 10-15 are capable of being executed in an order that differs from the illustrated serial and iterative manner of discussion. It is also envisioned that not all steps are required as described below.

Figure 10:
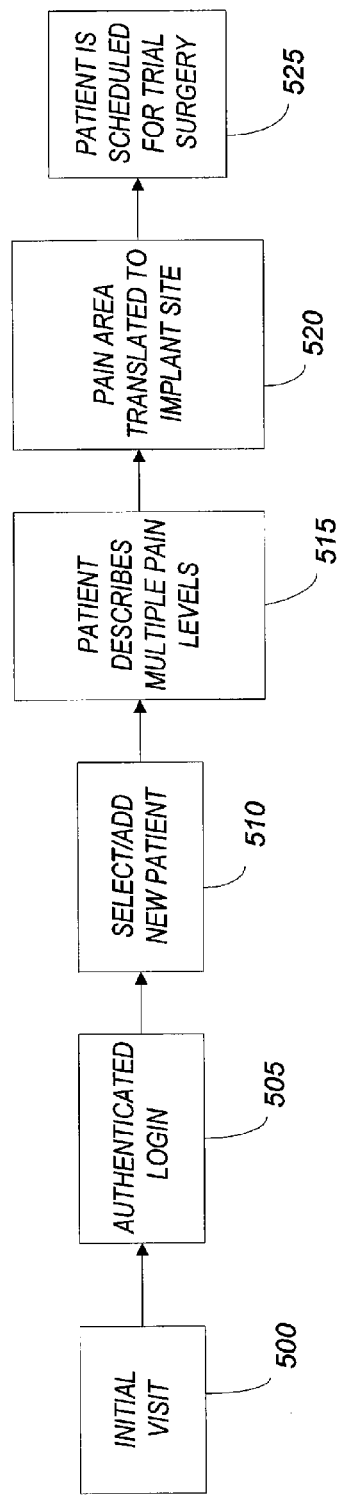
FIG. 10 is a flow diagram of a patient performing an initial visit with a clinician.

With reference to FIG. 10, the patient 105 performs an initial visit (block 500). The clinician working with the patient 105 logs into the CP 130 (block 505), and either selects a stored existing patient or adds a new patient to the CP 130 (block 510). The patient 105 then describes his pain area (block 515). Using the patient's description, implant sites for a future surgery (block 520) are determined. The patient 105 is then scheduled for trial surgery (block 525).

Figure 11:
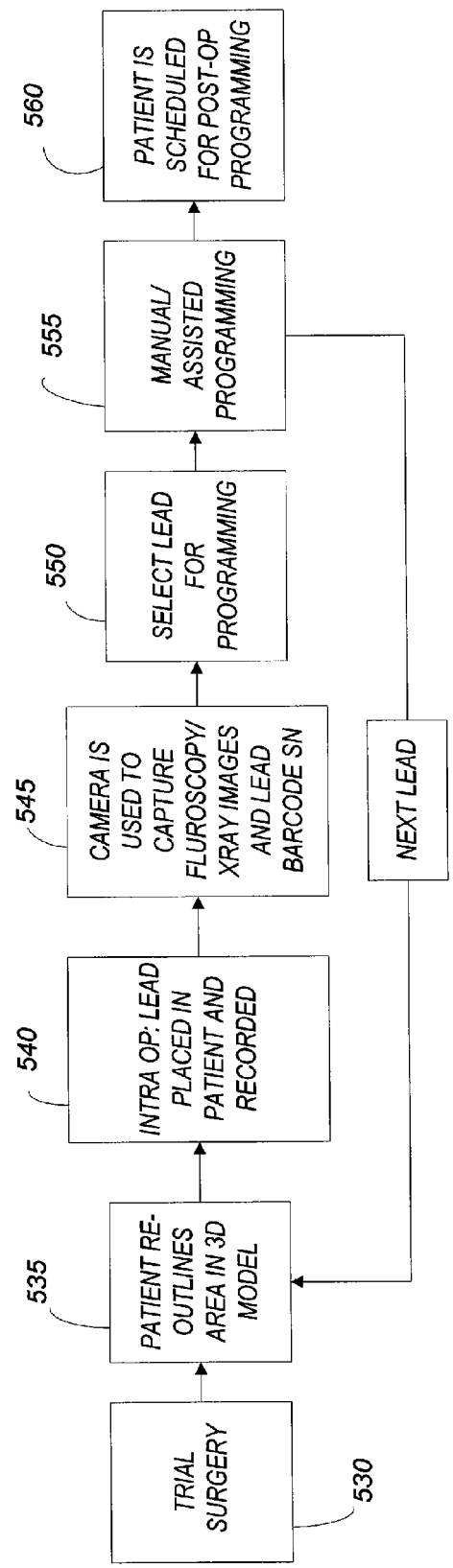
FIG. 11 is a flow diagram of a patient undergoing an initial visit followed by trial surgery procedure.
Figure 12:
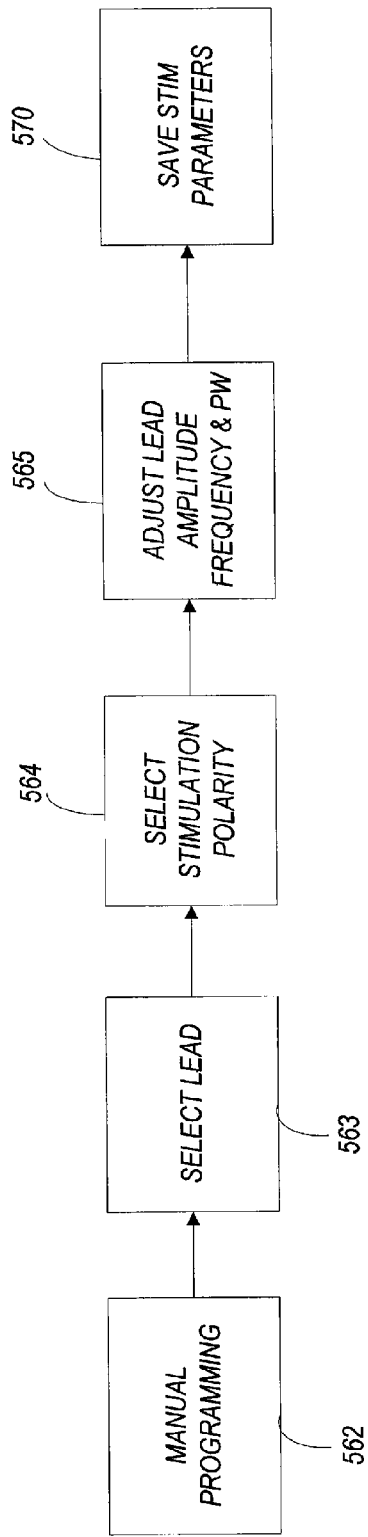
FIG. 12 is a flow diagram of the manual programming of a lead.
Figure 13:
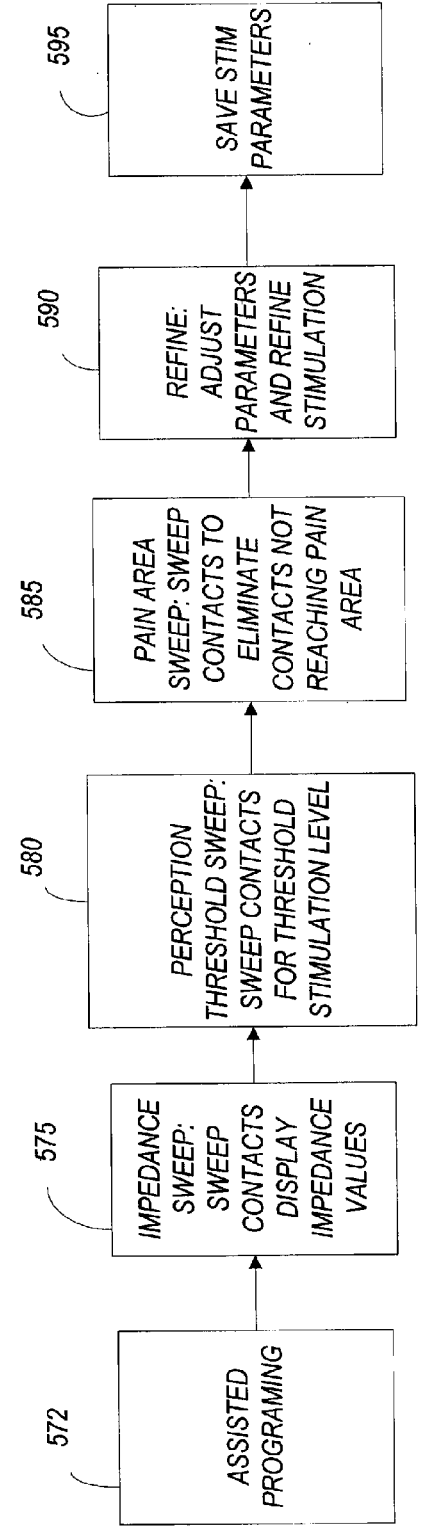
FIG. 13 is a flow diagram of the computer assisted programming of a lead.

Referring now to FIG. 11, the patient 105 returns for trial surgery (block 530). After obtaining the previously stored patient information, the patient 105 again describes his pain area (block 535) and the location for lead implant sites can be confirmed. During the procedure, one or more leads 110 are placed in the patient 105 and their respective locations recorded in the CP 130 (block 540). Further, the camera 380 can be used to capture images of the procedure, and capture/read barcode serial numbers of the leads 110 (block 545). It also envisioned that fluoroscopy/X-ray images can be recorded in the CP 130 as part of the procedure. The result of blocks 540 and 545 is that the CP 130 has a type, location, orientation, and other contextual information relating to the implanting of the lead 110. This provides a more robust and accurate programming of the lead 110.

Next (block 550), the clinician selects the lead 121 for programming. The programming can be manual or assisted (block 555), both of which are discussed below. The process can then be repeated for a next lead, or the patient is then scheduled for post-op programming (block 560).

Referring again to block 555, the clinician either manually or automatically programs the operation of the IPG 115 (which may also be an EPG) to provide electrical stimulation through the lead 110. With manual programming (FIG. 12, block 562), the clinician selects a lead (block 563), selects a stimulation polarity, which may be cathodal stimulation as it requires the least amount of current (voltage) to elicit a response (block 564), and manually adjusts pulse amplitude, frequency, and width of the electrical stimuli provided by the electrodes 150 (block 565). The patient 105 typically provides verbal responses to cues given by the clinician. This in particular is difficult and time consuming during a permanent implant where the patient has to be woken up from the general anesthesia and struggling to be cognitive with often speech impediments. This process can be very time consuming given the number of variables for each electrode/channel. The manual process also does not often result in a "best fit" for providing electrical stimulation treatment and relies significantly on the clinician's experience. The CP 130 saves the resulting protocol of the manually assisted programming (block 570).

With assisted programming (FIG. 13, block 572), the CP 130 establishes a protocol for providing electrical stimuli to the patient 105. More specifically, the assisted programming first performs three sweeps of the electrodes 150 to result in a best selection of the electrodes 150 for providing paresthesia. The first sweep (block 575) is an impedance sweep to determine a respective impedance between the IPG 115, connected lead, each electrode 150, and tissue. The impedances are displayed on the touch screen 375 and can be used by the clinician to help determine whether an electrode 150 falls in between an accepted impedance range. The second sweep (block 580) is a perception-threshold sweep to find the minimum threshold stimulation sensed by the patient 105 for each channel/electrode 150. The second sweep (block 580) is a perception-threshold sweep to find the minimum threshold. In one implementation, the stimulation sensed by the patient 105 for each channel/electrode 150 is cathodal polarity with the IPG 115 can being the anode. For an EPG, a reference electrode may represent the cathodal anode. The values of the perception-threshold sweep are used to normalize the initial sensation felt by the patient with each electrode 150. The last sweep (block 585) is a pain-area sweep to identify the optimal paresthesia electrodes to the pain area. Even more accurately, the pain-area sweep (block 585) eliminates contacts not reaching the pain area. The clinician can then repeat any of the sweeps and/or refine the paresthesia to the patient (block 590). The refining of the paresthesia can include adjusting parameters of electric stimulation through the electrodes identified in block 585, surrounding an electrode identified in block 585 with anode or cathode blocks, or shifting a pattern longitudinally or laterally, as is known in the art. After completion, the CP 130 saves the stimulation parameters (block 595). Further discussion regarding the CP 130 assisted programming will be provided below.

Before proceeding further, it should be noted that the contextual information relating to the implanting of the lead 110 (from blocks 540 and 545, above) can be used when programming the stimulation generator. That is, the contextual information can be used to exactly identify the lead 110, corresponding electrode array 120, orientation of the lead 110, the placement of the lead 110, etc. The CP 130 automatically accounts for this information when establishing the protocol. For a specific example, the CP allows for an anatomically correct placement of the stimulation lead, if the surgeon chooses to orient the lead in another way, such as antegrate or diagonal. The CP 130 accounts for this placement while performing the sweeps.

Figure 14:
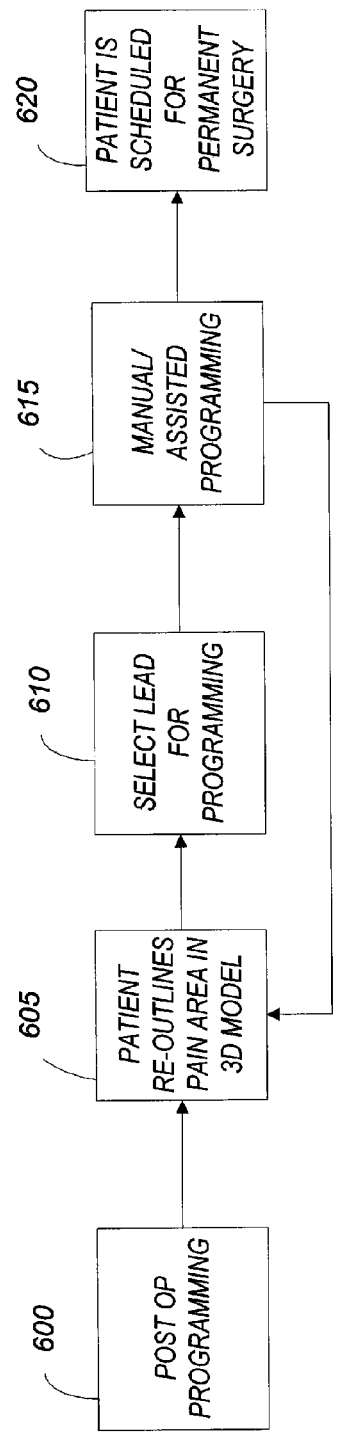
FIG. 14 is a flow diagram of a patient performing a post trial programming session.
Figure 15:
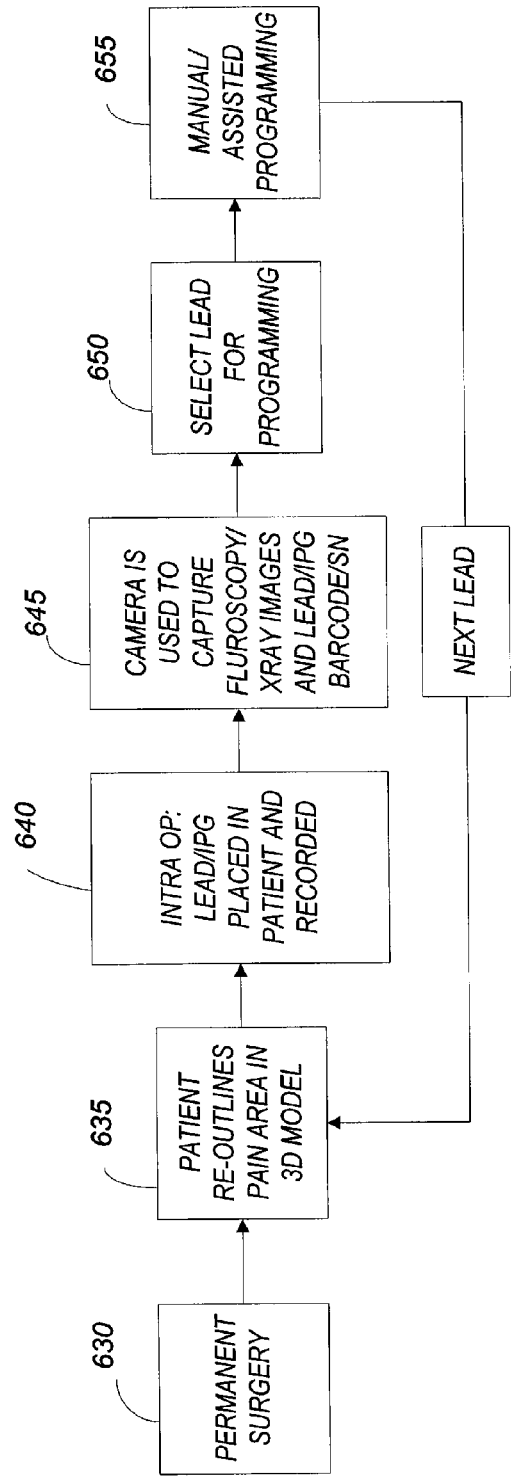
FIG. 15 is a flow diagram of a patient undergoing a permanent surgery procedure.

Referring now to FIG. 14, the patient 105 returns for post operation programming (block 600). Again, the patient 105 can describe the pain he is experiencing (block 605). The clinician then selects a lead 110 for programming (block 610) and performs manual or assisted programming for the lead 110 (block 615). The patient is then scheduled for permanent surgery (block 620).

With permanent surgery (FIG. 15, block 630), the operation is similar to the trial surgery except the IPG 115 is typically inserted into the patient. At block 635, the patient again describes his pain area (block 635), which typically corresponds to the previously described pain area, and the location for lead implant sites can be confirmed. During the procedure, one or more leads 110 are placed in the patient and recorded in the CP (block 640). Also, the IPG 115 is placed in the patient and recorded in the CP 130 (block 640). The camera 380 can be used to capture images of the procedure, capture/read barcode serial numbers of the leads 110, and capture/read barcode serial numbers of the IPG (block 645). Further, fluoroscopy/X-ray images can be recorded in the CP 130, similar to the trial surgery, to help record the procedure (block 645). Next (block 650), the clinician selects the lead 110 for programming. The programming can be manual or assisted (block 655), as already discussed. The process can then be repeated for a next lead 110.

Accordingly, FIGS. 11-15 provide a process for treating a patient using the SCS 100. FIGS. 16-19 provide more detailed processes for performing computer assisted stimulation programming (CASP) using the CP 130. The steps discussed in connection with FIGS. 16-19 will be discussed in an iterative manner for descriptive purposes. Various steps described herein with respect to the process of FIGS. 16-19 are capable of being executed in an order that differs from the illustrated serial and iterative manner of discussion. It is also envisioned that not all steps are required as described below.

Figure 16:
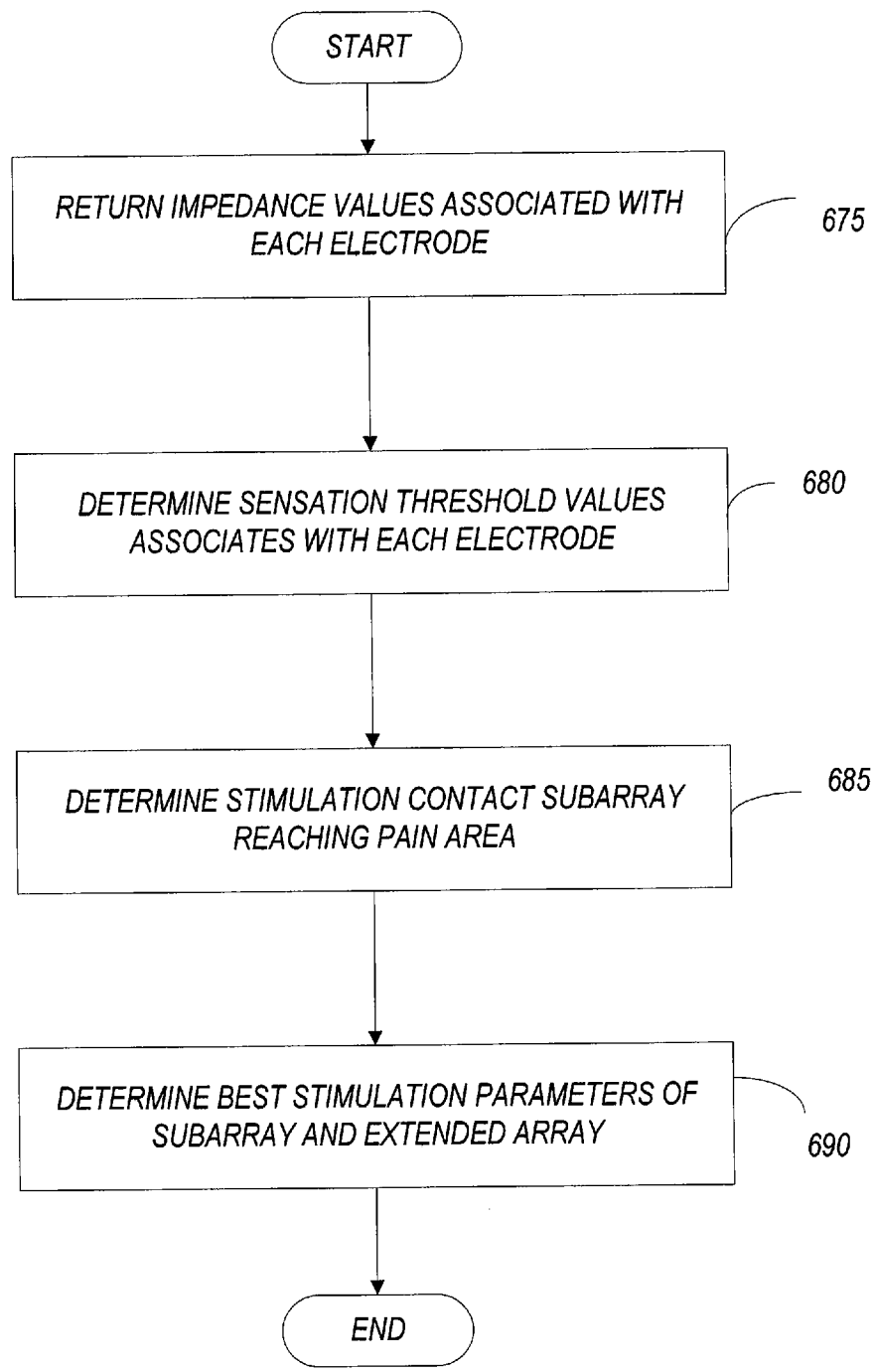
FIG. 16 is a flow diagram of an exemplary computer assisted stimulation programming process for use with the spinal cord stimulation system of FIG. 1.
Figure 17:
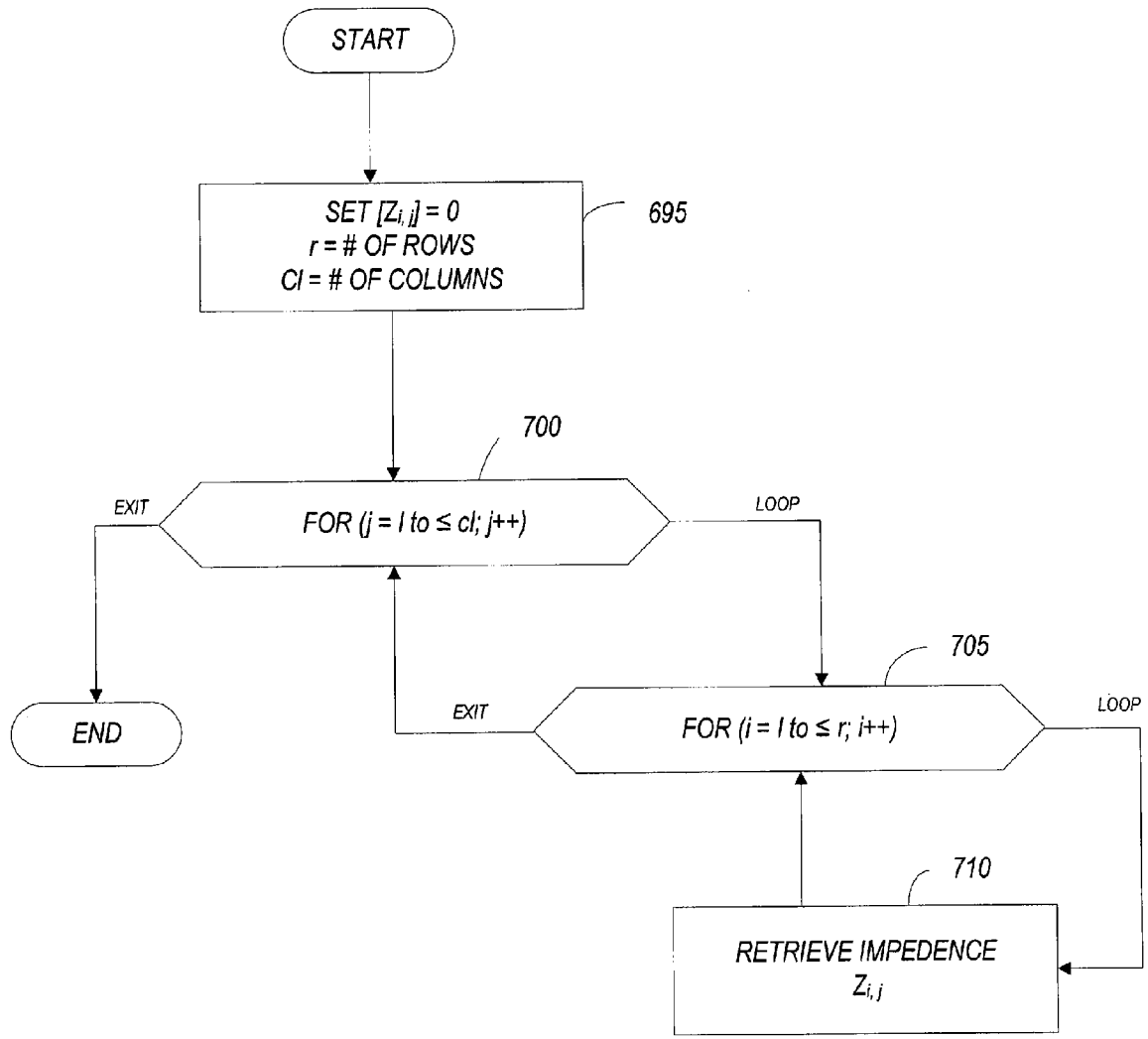
FIG. 17 is a flow diagram of an exemplary process for determining impedance values associated with each electrode.
Figure 18A:
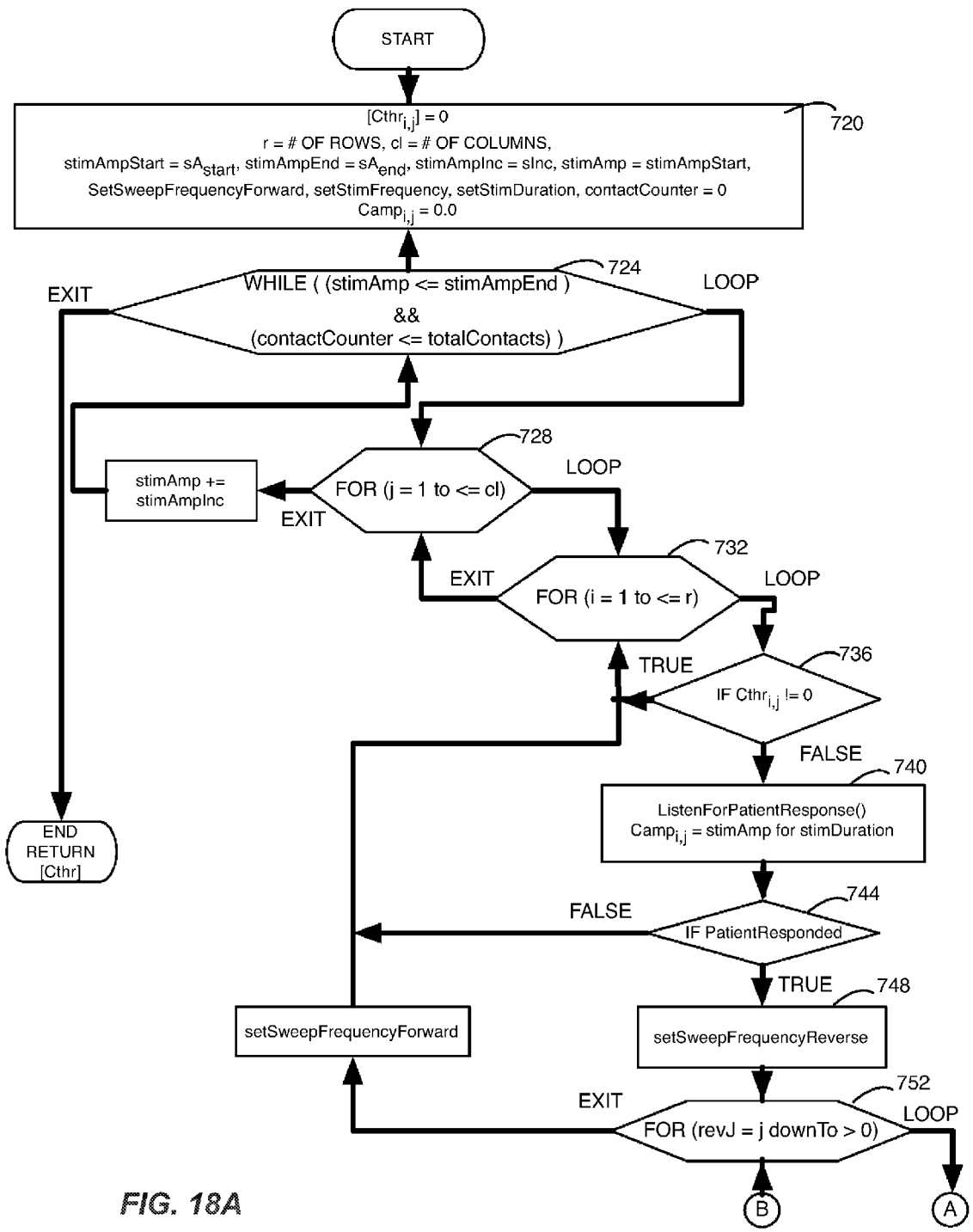
FIGS. 18A and 18B are a flow diagram of an exemplary process for determining perception threshold values associated with each electrode.
Figure 18B:
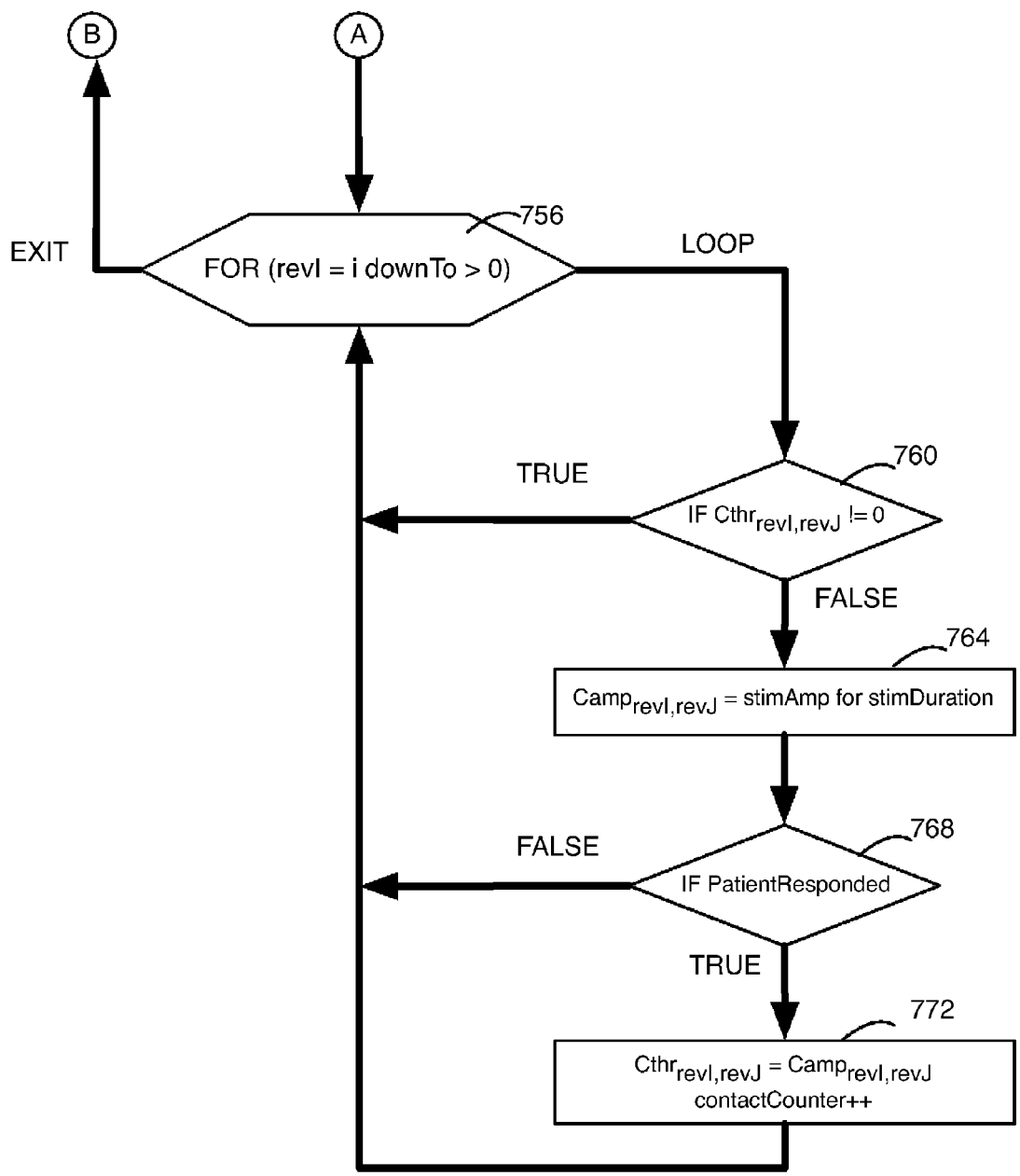
Figure 19:
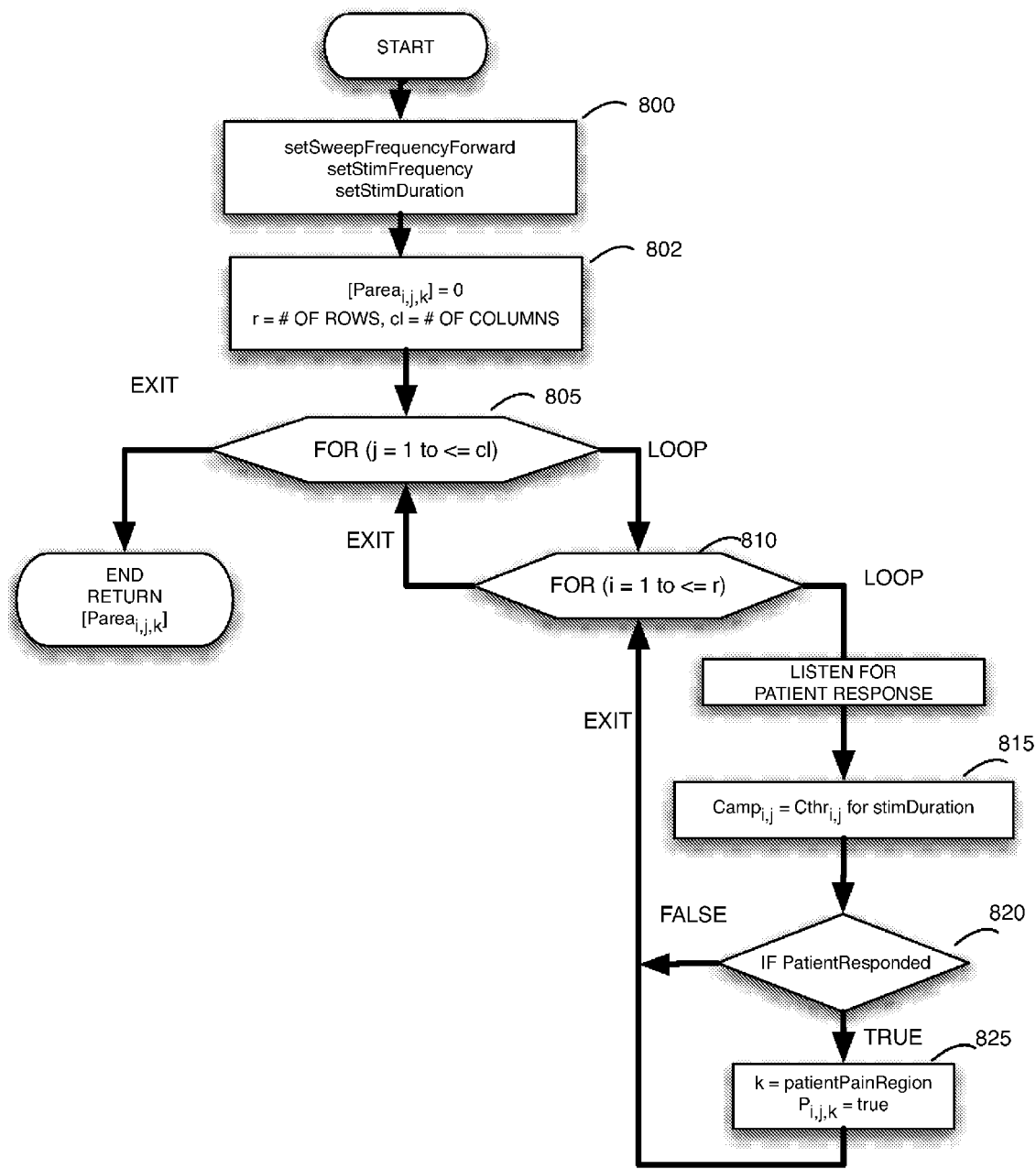
FIG. 19 is a flow diagram of an exemplary process for determining a stimulation electrode sub-array reaching a pain area of the patient.

FIG. 16 shows four exemplary sub-processes of the CASP process. The first process (block 675) retrieves impedance values of the electrodes 150 in a lead 110. In order to perform the process 675, the clinician identifies the lead 110 to the CP 130. The CP 130 knows the arrangement of the electrode array 120, as previously discussed, for the lead 110 once the lead 110 is identified. One exemplary pseudo code and related flow chart for process 675 is shown below and in FIG. 17, respectively. This pseudo code assumes impedance between the contact $Z_{i,j}$, connected lead, the can of the IPG 115, and tissue. However, other impedance combinations are possible between contacts $Z_{i,j}$ and $Z_{k,l}$,
where (k=1:r); (l=1:cl) and (k!=i)∨(l!=j);

```
Require: EPG or IPG communication established
1: [Z_{i,j}] ← 0              >setting impedance array to zero
2: r ← number of rows         >number of contacts in lead latitudinally
3: cl ← number of columns     > number of contacts in lead longitudinally
4: for j = 1 to ≤ cl do
5:    for i = 1 to ≤ r do
6:       Z_{i,j} ← retrieve impedance of contact i, j   >computed by
                                                         IPG/EPG
7:    end for
8: end for
9: return [Z_{i,j}]
```

First, the array $[Z_{i,j}]$ is set to zero, the number of rows r is identified, and the number of columns cl is identified (block 695). The array $[Z_{i,j}]$ corresponds to an array representing the electrode array 120. The letter i represents the i-th row from 1 to r rows. The letter j represents the j-th column from 1 to j columns. As discussed previously, the representative array $[Z_{i,j}]$ can represent many electrode arrays, including complex electrode array configurations having "dummy" addresses with "null" values. Therefore, not every address of the array $[Z_{i,j}]$ may include a value. Returning to FIG. 17, the process performs a first for-loop (block 700) for the columns and a second for-loop (block 705) for the rows of the array $[Z_{i,j}]$. The two loops allow the process to progress through each electrode 150 of the electrode array 120 to obtain an impedance value associated with each channel (block 710). Each impedance value relates to the impedance between the can 220 of the IPG 115, the connected lead, tissue, for example, and a respective electrode 150. The process of FIG. 17 helps to determine that the impedance values of lead 110 fall within acceptable ranges, necessary to provide electrical stimulation to the nerves.

Referring back to FIG. 16, the second process (block 680) determines the perception-threshold values of the electrodes 150 in a lead 110. During the process, the patient 105 provides feedback using the PFD 145 when the patient 105 senses a stimulation, such as a paresthesia sensation. One exemplary pseudo code and related flow chart for process 680 is shown below and in FIG. 18, respectively.

```
Require: EPG or IPG communication established
Ensure: Impedance of each contact retrieved
 1: [Cthr_{i,j}] ← 0              >setting contact stim threshold array to
                                   zero
 2: r ← number of rows            >number of contacts in lead latitudinally
 3: cl ← number of columns        >number of contacts in lead
                                   longitudinally
 4: stimAmpStart ← sA_{start}     >initial stim amplitude
 5: stimAmpEnd ← sA_{end}         >ending stim amplitude
 6: stimAmpInc ← sInc             >stim amplitude increment
 7: stimAmp ← stimAmpStart        >beginning stimulation amplitude
 8: setSweepFrequencyForward      >activation frequency
 9: setStimFrequency              >stimulation in pulses per seconds
10: setStimDuration               >duration of stimulation per contact
11: contactCounter ← 0
12: Camp_{ij} ← 0
13: while stimAmp ≤ stimAmpEnd && contactCounter ≤ totalContacts
    do
14:    for j = 1 to cl do
15:       for i = 1 to r do
16:          if Cthr_{i,j} ≠ 0 then   >ignore contacts that already have
                                        thresholds established
17:             continue
18:          end if
19:          listenForPatientResponse( )
20:          Camp_{i,j} ← stimAmp for stimDuration  >start stimulation
21:          if patientResponded then
22:             setSweepFrequencyReverse, startSweepReverse
23:             for revJ = j downto revJ > 0 do
24:                for revI = i downto revI > 0 do
25:                   if Cthr_{revI,revJ} ≠ 0 then>ignore contacts that already
                         have thresholds established
26:                      continue
27:                   end if
28:                   Camp_{revI,revJ} ← stimAmp for stimDuration > start
                         stimulation
29:                   if patientResponded then
30:                      Cthr_{revI,revJ} ← Camp_{revI,revJ}
31:                      contactCounter ++
32:                   endif
33:                end for
34:             end for
35:          end if
36:          setSweepFrequencyForward
37:       end for
38:    end for
39:    stimAmp+ ← stimAmpInc
40: end While
41: return [Cthr_{i,j}]
```

First the array $[Cthr_{i,j}]$ is set to zero, the number of rows r is identified and the number of columns cl is identified (block 720). Also, the initial stimulation amplitude stimAmpStart, the ending stimulation amplitude stimAmpEnd, and the stimulation amplitude increment stimAmpInc are identified; the variable stimAmp is set; and the counter contactCounter is set. Also, the forward sweep frequency setSweepFrequencyForward, the stimulation frequency setStimFrequency, the duration of stimulation setStimDuration are established and the stimulation $Camp_{ij}$ is tuned off (block 720).

The CASP process performs a while-loop to determine the perception-threshold values of the electrodes 150. The while-loop is performed while the stimAmp value is less than the threshold stimAmpEnd and each contact does not have a perception-threshold value (block 724). The while-loop includes two for-loops: a first for-loop for the columns of the array (block 728) and a second for-loop for the rows of the array (block 732). The two loops allow the CASP process to progress through each electrode 150 of the electrode array 120. While performing the loops, the process determines whether the perception array does not have a perception value for the i-th row and the j-th column (block 736). If the array location has a perception-threshold value, then the process returns to block 732. Otherwise, the process continues.

Before proceeding further, it should be noted that the CASP process automatically and systematically progress through the electrodes 150. In addition, as shown by block 736, the CASP process "skips" or passes over an electrode $C_{i,j}$ once a perception threshold $Cthr_{i,j}$ is identified for the electrode 150. However, the sweeping of the electrodes 150 is still automated and systematic even when this skip process occurs.

Referring now to block 740, the contact amplitude $Camp_{i,j}$ is set to the stimulation amplitude stimAmp, the process pauses for a duration. At the same time the CASP is monitoring for a patient response. For the implementation discussed herein, the stimulation amplitude is a current amplitude. However, a voltage amplitude or other variable (pulse shape, frequency, width, etc.) can be used and adjusted in place of the current amplitude. If the patient 105 feels a sensation, then they provide feedback to the CP 130 via the PFD 145 (block 744). If a patient 105 response is detected then the process proceeds to block 748. Otherwise, the CASP process continues to proceed through the for-loops.

When a patient 105 provides feedback indicating a response, a reverse frequency is set (block 748) and the sweep is reversed (starting at block 752). More specifically, for the CASP process discussed herein, the process proceeds quickly through the electrode array 120 and a delayed reaction from the patient 105 is expected. By performing a reverse sweep, the CASP process more accurately confirms a response. The CASP process initiates two for-loops 752-756 in a reverse sweep direction. While performing the reverse sweep, the process "skips" or passes over electrodes 150 having perception thresholds (block 760). The contact amplitude $Camp_{revI, revJ}$ is set to the stimulation amplitude stimAmp, the process pauses for a duration (block 764). If a patient 105 feels a sensation, then they provide feedback to the CP 130 with the PFD 145. If a patient 105 response is detected (768), then the process proceeds to block 772. Otherwise, the CASP process continues to proceed through the for-loops 752 and 756. At block 772, the perception-threshold value is set for $Cthr_{revI, revJ}$ and the contactCounter increments.

Upon completion of the perception threshold sweep, perception thresholds $[Cthr_{i,j}]$ are established for each contact 150. The values of the perception-threshold sweep are used to normalize the initial sensation felt by the patient with each channel/electrode 150.

Referring again to FIG. 16, the third process (block 685) performs a pain-area sweep to determine the best electrode(s) 150 for stimulating neurons to the affected pain area. During this process, the patient 105 again provides feedback using the PFD 145 when the patient 105 senses a defined stimulation. One exemplary pseudo code and related flow chart for process 685 is shown below and in FIG. 19, respectively.

```
Require: [Cthr_{i,j}] ≠ 0          >threshold array is not empty
Ensure: stimulation contacts that cover pain
  1:    [Parea_{i,j,k}] ← false
  2:    setSweepFrequencyForward  >activation frequency
  3:    setStimFrequency           >stimulation in pulses per seconds
  4:    setStimDuration            >duration of stimulation per contact
  5:    r ← number of rows         >number of contacts in lead
                                    latitudinally
  6:    cl ← number of columns    >longitudinal columns
  7:    for: j = 1 to ≤ r do
  8:        for i = 1 to ≤ cl do
  9:            listenForPatientResponse( )
 10:            Camp_{i,j} ← Cthr_{i,j} for stimDuration >start stimulation
 11:            if patientResponse then
 12:                k ← patientPainRegion > patient locates where pain
                    region is
 13:                PainA_{i,j,k} ← true
 14:            end if
 15:        end for
 16:    end for
 17:    return [Parea_{i,j,k}]
```

First, the forward sweep frequency setSweepFrequencyForward, the stimulation frequency setStimFrequency, the duration of stimulation setStimDuration are established and the stimulation $Camp_{i,j}$ is tuned off (block 800). Next, the number of rows r is identified, the number of columns cl is identified, and the array $[Parea_{i,j,k}]$ is set to false (block 802). The CASP process then automatically and systematically progresses through the electrodes 150. A first for-loop (block 805) for the columns of the area and a second for-loop (block 810) for the rows of the array are swept. While performing the loops, the electrode $Camp_{i,j}$ is set to the threshold $Cthr_{i,j}$ which may be set from the prior perception-threshold sweep (block 815). The process pauses for a duration. If the electrode 150 stimulates neurons related to the pain area, then the patient 105 provides feedback to the CP 130 via the PFD 145. If a patient 105 response is detected (block 820) then the process proceeds to block 825. Otherwise, the CASP process continues the automated and systematic sweep through the electrodes 150. At block 825, the patient identifies the paresthesia area (k) the stimulation is reaching and contact i,j in the array $[Parea_{i,j,k}]$ is set to true.

In some implementations, when a patient 105 provides feedback indicating a response to the stimulation that reaches the pain area, the sweep can be repeated multiple times over. The resulting multitude pain area arrays can be compared to verify consistent patient response. However, the exemplary process shown in FIG. 19 does not include the repeated sweep.

At the end of the pain-area sweep, the CP 130 identifies the best electrode(s) 150 for stimulating neurons to the affected pain area, i.e., to provide paresthesia to the affected pain areas. It is envisioned that the process of performing the perception threshold sweeps and pain area sweeps can be performed in less than thirty minutes, and preferably in less than ten minutes. The time can vary based on the sweep speed and delay times used during the sweep. The CP 130 can then isolate the resulting best electrodes and refine the stimulation parameters (amplitude, frequency, pulse width) to result in an optimal pattern as has been previously done in prior SCS systems (block 690 of FIG. 16).

Thus, the invention provides, among other things, useful and systems and methods for providing electrical stimulation to a neural tissue of a patient. Various features and advantages of the invention are set forth in the following claims.

What is claimed is:

1. A method of establishing a protocol for providing therapeutic electrical stimulation with a stimulation system for treating a patient, the stimulation system comprising an electrical stimulation generator, one or more implanted medical leads coupled to the electrical stimulation generator, the one or more implanted medical leads including a plurality of electrodes, a programmer configured to communicate with the electrical stimulation generator, and a patient feedback device configured to communicate with the programmer, the method comprising:
    initiating automated and systematic sweeping through the plurality of electrodes with electrical stimuli provided by the electrical stimulation generator in response to communication from the programmer, wherein the initiating step includes
        performing a first automated and systematic sweep through the plurality of electrodes to determine a respective perception threshold associated with each electrode, the first automated and systematic sweep including
            providing a first electrical stimulus having a first amplitude to a first electrode, waiting a time period for detecting patient feedback after providing the first electrical stimulus, then providing a second electrical stimulus having the first amplitude to a second electrode, waiting the time period for detecting patient feedback after providing the second electrical stimulus, then providing a third electrical stimulus having the first amplitude to a third electrode, waiting the time period for detecting patient feedback after providing the third electrical stimulus, and repeating the providing and waiting steps with the first, second, and third electrical stimuli having a second amplitude greater than the first amplitude, and performing a second automated and systematic sweep through the plurality of electrodes to determine an electrode that is associated with a pain area of the patient, the second automated and systematic sweep including providing a fourth electrical stimulus having a third amplitude to the first electrode, waiting the time period for detecting patient feedback after providing the fourth electrical stimulus, then providing a fifth electrical stimulus having a fourth amplitude to the second electrode, waiting the time period for detecting patient feedback after providing the fifth electrical stimulus, then providing a sixth electrical stimulus having a fifth amplitude to the third electrode, waiting the time period for detecting patient feedback after providing the sixth electrical stimulus, and wherein the fourth, fifth, and sixth electrical stimuli are based on the respective perception thresholds from the first automated and systematic sweep;

determining whether the patient provided feedback with the patient feedback device while performing the automated and systematic sweeping, wherein the determining step includes detecting patient feedback with the patient feedback device while performing the first automated and systematic sweep, and detecting patient feedback with the patient feedback device while performing the second automated and systematic sweep; and creating the protocol for providing therapeutic electrical stimulation to treat the patient based on the automated and systematic sweeping through the plurality of electrodes and the patient provided feedback, wherein the creating step includes developing the protocol for providing therapeutic electrical stimulation to treat the patient based on the second automated and systematic sweep and the detected patient feedback.

2. The method of claim 1, wherein the automated and systematic sweeping includes automatically generating at least one electrical stimulus over a time period corresponding to each electrode in a systematic sequence.

3. The method of claim 2, wherein the respective electrical stimulus includes a pulse having a constant voltage.

4. The method of claim 2, wherein the respective electrical stimulus includes a pulse having a constant current.

5. The method of claim 2, wherein the creating the protocol includes adjusting at least one of amplitude, frequency, pulse width, pulse shape, and stimulation type of an electrical stimulus to refine the protocol.

6. The method of claim 2, wherein the creating the protocol further includes modifying the enablement or disablement of one of the plurality of electrodes to refine the protocol.

7. The method of claim 1, wherein the stimulation system includes a spinal cord stimulation system and the stimulation generator includes a pulse generator, and wherein the therapeutic electrical stimulation includes providing paresthesia for the patient.

8. The method of claim 1, and further comprising performing a third automated and systematic sweep through the plurality of electrodes to determine a respective impedance associated with each electrode.

9. The method of claim 1, wherein the second automated and systematic sweep includes automatically generating a respective electrical stimulus having a relation to the perception threshold of the electrodes, respectively, for a time period in a systematic sequence.

10. The method of claim 1, wherein the detecting patient feedback while performing the first automated and systematic sequence results in the method further comprising pausing the first automated and systematic sweep;

performing a third automated and systematic sweep through the plurality of electrodes in a reverse systematic sequence from the systematic sequence;

detecting patient feedback with the patient feedback device while performing the third automated and systematic sweep; and reinitiating the first automated and systematic sweep.

11. The method of claim 1, further comprising:

storing a location of the patient for implanting the one or more leads to receive stimulation; and image capturing an aspect of the one or more leads.

12. The method of claim 11, and further comprising image capturing an aspect of the pulse generator.

13. The method of claim 11, wherein the initiating the automated and systematic sweep includes automatically generating a respective electrical stimulus for a time period with each electrode in a systematic sequence.

14. The method of claim 11, wherein the initiating the automated and systematic sweep includes performing an automated and systematic sweep through the plurality of electrodes to determine a respective perception threshold associated with each electrode.

15. The method of claim 11, wherein the initiating the automated and systematic sweep includes performing an automated and systematic sweep through the plurality of electrodes to determine an electrode that is associated with a pain area.

16. The method of claim 11, wherein the initiating the automated and systematic sweep includes performing a first automated and systematic sweep through the plurality of electrodes to determine a respective perception threshold associated with each electrode, and performing a second automated and systematic sweep through the plurality of electrodes to determine an electrode that is associated with a pain area.

17. A method of establishing a protocol for providing therapeutic electrical stimulation with a stimulation system for treating a patient, the stimulation system comprising an electrical stimulation generator, one or more implanted medical leads coupled to the electrical stimulation generator, the one or more implanted medical leads including a plurality of electrodes, a programmer configured to communicate with the electrical stimulation generator, and a patient feedback device configured to communicate with the programmer, the method comprising:

initiating automated and systematic sweeping through the plurality of electrodes with electrical stimuli provided by the electrical stimulation generator in response to communication from the programmer, wherein the automated and systematic sweeping includes automatically generating at least one electrical stimulus over a time period corresponding to each electrode in a systematic sequence, including
   providing a first electrical stimulus with a first amplitude to a first electrode,
   then providing a second electrical stimulus with the first amplitude to a second electrode, and
   then providing a third electrical stimulus with the first amplitude to a third electrode;
determining whether the patient provided feedback with the patient feedback device while performing the automated and systematic sweeping, wherein the determining step includes receiving a feedback signal from the feedback device;
pausing the automatically generating the at least one electrical stimulus in the systematic sequence;
automatically generating a second at least one electrical stimulus over a second time period with the plurality of electrodes in a reverse systematic sequence from the systematic sequence, including
   providing the second electrical stimulus with the first amplitude to the second electrode,
   then providing the first electrical stimulus with the first amplitude to the first electrode;
determining whether the patient provided feedback with the patient feedback device while automatically generating the second at least one electrical stimulus; and
creating the protocol for providing therapeutic electrical stimulation to treat the patient based on the automated and systematic sweeping through the plurality of electrodes, and the patient provided feedback.

18. The method of claim 17, wherein the initiating the automated and systematic sweeping includes performing an automated and systematic sweep through the plurality of electrodes to determine a respective perception threshold associated with each electrode.

19. The method of claim 17, wherein the initiating the automated and systematic sweeping includes performing an automated and systematic sweep through the plurality of electrodes to determine an electrode that is associated with a pain area.

20. The method of claim 17, wherein the initiating the automated and systematic sweeping includes performing a first automated and systematic sweep through the plurality of electrodes to determine a respective perception threshold associated with each electrode, and performing a second automated and systematic sweep through the plurality of electrodes to determine an electrode that is associated with a pain area.

21. The method of claim 20, wherein the first automated and systematic sweep and the second automated and systematic sweeps are performed in less than thirty minutes.

* * * * *